US010973822B2

(12) United States Patent
Gandhi et al.

(10) Patent No.: US 10,973,822 B2
(45) Date of Patent: Apr. 13, 2021

(54) COMBINATION THERAPY FOR TREATMENT OF HEMATOLOGICAL CANCERS AND SOLID TUMORS

(71) Applicant: Celgene Corporation, Summit, NJ (US)

(72) Inventors: Anita Gandhi, Bernardsville, NJ (US); Hsiling Chiu, Livingston, NJ (US); Michael Pourdehnad, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 366 days.

(21) Appl. No.: 15/741,130

(22) PCT Filed: Jul. 1, 2016

(86) PCT No.: PCT/US2016/040718
§ 371 (c)(1),
(2) Date: Dec. 29, 2017

(87) PCT Pub. No.: WO2017/004532
PCT Pub. Date: Jan. 5, 2017

(65) Prior Publication Data
US 2018/0193342 A1 Jul. 12, 2018

Related U.S. Application Data

(60) Provisional application No. 62/340,972, filed on May 24, 2016, provisional application No. 62/308,055, filed on Mar. 14, 2016, provisional application No. 62/245,916, filed on Oct. 23, 2015, provisional application No. 62/188,404, filed on Jul. 2, 2015.

(51) Int. Cl.
A61K 31/517 (2006.01)
A61P 35/00 (2006.01)
A61K 31/706 (2006.01)
A61K 39/395 (2006.01)
A61K 39/00 (2006.01)

(52) U.S. Cl.
CPC .......... A61K 31/517 (2013.01); A61K 31/706 (2013.01); A61K 39/3955 (2013.01); A61K 39/39558 (2013.01); A61P 35/00 (2018.01); A61K 2039/505 (2013.01); A61K 2039/507 (2013.01); A61K 2039/545 (2013.01)

(58) Field of Classification Search
CPC ........... A61K 31/706; A61K 31/517; A61K 2300/00; A61K 2039/505; A61P 35/00; A61P 35/02
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,134,127 | A | 7/1992 | Stella et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,733,566 | A | 3/1998 | Lewis |
| 5,811,097 | A | 9/1998 | Allison et al. |
| 5,855,887 | A | 1/1999 | Allison et al. |
| 6,051,227 | A | 4/2000 | Allison et al. |
| 6,207,157 | B1 | 3/2001 | Gu et al. |
| 6,682,736 | B1 | 1/2004 | Hanson et al. |
| 6,984,720 | B1 | 1/2006 | Korman et al. |
| 7,488,802 | B2 | 2/2009 | Collins et al. |
| 7,605,238 | B2 | 10/2009 | Korman et al. |
| 7,635,700 | B2 | 12/2009 | Muller et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,492,395 | B2 | 7/2013 | Muller et al. |
| 8,802,685 | B2 | 8/2014 | Muller et al. |
| 8,906,932 | B2 | 12/2014 | Muller et al. |
| 8,921,385 | B2 | 12/2014 | Muller et al. |
| 9,067,912 | B2 | 6/2015 | Ruchelman et al. |
| 9,096,573 | B2 | 8/2015 | Muller et al. |
| 9,119,854 | B2 | 9/2015 | Chopra et al. |
| 9,249,121 | B2 | 2/2016 | Muller et al. |

(Continued)

FOREIGN PATENT DOCUMENTS

WO WO 2003/042402 A2 5/2003
WO WO 2008/156712 A1 12/2008
(Continued)

OTHER PUBLICATIONS

Jacques et al (PNAS, 2015, pp. E1471-E1470) (Year: 2015).*
Hagnar et al (Blood, 2015, vol. 126, pp. 779-789) (Year: 2015).*
Sznol and Chen (Clinical Cancer Research, 2013, vol. 19, pp. 1021-1034) (Year: 2013).*
Topalian et al (Current Opinion in Immunology, 2012, vol. 24, pp. 207-212) (Year: 2012).*
Postow et al (Journal of Clinical Oncology, e-pub Jan. 20, 2015, vol. 33, pp. 1974-1982) (Year: 2015).*
Sondergeld et al (Clinical Advances in Hematology & Oncology, 2015, vol. 13, pp. 599-609) (Year: 2015).*
(Continued)

Primary Examiner — Karen A. Canella
(74) Attorney, Agent, or Firm — Jones Day

(57) ABSTRACT

Provided herein are methods for treating, preventing, and/or managing hematological cancers and solid tumors using combination therapy of 3-(5-amino-2-4-oxo-4H-quinazolin-3-yl)-piperidine-2,6-dione and checkpoint inhibitors.

69 Claims, 13 Drawing Sheets

(56) References Cited

U.S. PATENT DOCUMENTS

| | | |
|---|---|---|
| 9,266,858 B2 | 2/2016 | Ruchelman et al. |
| 9,303,014 B2 | 4/2016 | Ruchelman et al. |
| 9,586,929 B2 | 3/2017 | Muller et al. |
| 9,682,952 B2 | 6/2017 | Man et al. |
| 9,732,064 B2 | 8/2017 | Muller et al. |
| 9,751,853 B2 | 9/2017 | Muller et al. |
| 9,834,538 B2 | 12/2017 | Muller et al. |
| 9,969,713 B2 | 5/2018 | Muller et al. |
| 2012/0230983 A1 | 9/2012 | Muller et al. |
| 2012/0232100 A1 | 9/2012 | Muller et al. |
| 2014/0148473 A1 | 5/2014 | Gandhi et al. |
| 2014/0228382 A1 | 8/2014 | DeWitt |
| 2014/0328832 A1 | 11/2014 | Chopra et al. |
| 2015/0126538 A1 | 5/2015 | Muller et al. |
| 2015/0196562 A1 | 7/2015 | Bhat |
| 2016/0136167 A1 | 5/2016 | Gandhi et al. |
| 2017/0056323 A1 | 3/2017 | Walters et al. |
| 2017/0157123 A1 | 6/2017 | Hagner et al. |
| 2017/0165266 A1 | 6/2017 | Gandhi et al. |
| 2017/0128448 A1 | 11/2017 | Pourdehnad et al. |
| 2017/0369471 A1 | 12/2017 | Muller et al. |
| 2018/0055844 A1 | 3/2018 | Muller et al. |
| 2018/0093965 A1 | 4/2018 | Man et al. |
| 2018/0118713 A1 | 5/2018 | Muller et al. |

FOREIGN PATENT DOCUMENTS

| | | | |
|---|---|---|---|
| WO | WO 2010/036959 A2 | 4/2010 | |
| WO | WO 2010/089411 A2 | 8/2010 | |
| WO | WO 2011/066342 A2 | 6/2011 | |
| WO | WO 2011/082400 A2 | 7/2011 | |
| WO | WO 2011/159877 A2 | 12/2011 | |
| WO | WO 2011/161699 A2 | 12/2011 | |
| WO | WO-2012125459 A1 * | 9/2012 | ........... A61K 31/352 |
| WO | WO 2014/039421 A1 | 3/2014 | |
| WO | WO 2014/039960 A1 | 3/2014 | |
| WO | WO 2015/069770 A1 | 5/2015 | |

OTHER PUBLICATIONS

The abstract of Stein et al (Blood, 2014, vol. 124, No. 21, p. 623) (Year: 2014).*

Topp et al (Blood, 2012, vol. 120, pp. 5185-5187) (Year: 2012).*

The abstract of Sangro et al (Journal of Clinical Oncology, 2013, vol. 31, Nol. 15, abstract No. TPS3111) (Year: 2013).*

Ansell et al., "PD-1 blockade with nivolumab in relapsed or refractory Hodgkin's lymphoma," *N. Engl. J. Med.*, 372(4):311-319 (2015).

Berger et al., "Phase I safety and pharmacokinetic study of CT-011, a humanized antibody interacting with PD-1, in patients with advanced hematologic malignancies," *Clin. Cancer Res.*, 14(10):3044-3051 (2008).

Brignone et al., "A soluble form of lymphocyte activation gene-3 (IMP321) induces activation of a large range of human effector cytotoxic cells," *J. Immunol.*, 179(6):4202-4211 (2007).

Bruix et al., "Focus on hepatocellular carcinoma," *Cancer Cell*, 5(3):215-219 (2004).

Camicia et al., "Novel drug targets for personalized precision medicine in relapsed/refractory diffuse large B-cell lymphoma: a comprehensive review," *Mol. Cancer*, 14:207 (2015).

Carstensen, *Drug Stability: Principles & Practices*, Second Edition, Marcel Dekker, New York, NY, pp. 379-380 (1995).

Fourcade et al., "Upregulation of Tim-3 and PD-1 expression is associated with tumor antigen-specific CD8+ T cell dysfunction in melanoma patients," *J. Exp. Med.*, 207(10):2175-2186 (2010).

Francisco et al., "The PD-1 pathway in tolerance and autoimmunity," *Immunol. Rev.*, 236:219-242 (2010).

Hamanishi et al., "Programmed cell death 1 ligand 1 and tumor-infiltrating CD8+ T lymphocytes are prognostic factors of human ovarian cancer," *Proc. Natl. Acad. Sci. USA*, 104(9):3360-3365 (2007).

Hanahan et al., "Hallmarks of cancer: the next generation," *Cell*, 144(5):646-674 (2011).

Hodi et al., "Improved survival with ipilimumab in patients with metastatic melanoma," *N. Engl. J. Med.*, 363(8):711-723 (2010).

Iwai et al., "Involvement of PD-L1 on tumor cells in the escape from host immune system and tumor immunotherapy by PD-L1 blockade," *Proc. Natl. Acad. Sci. USA*, 99(19):12293-12297.

Loo et al., "Development of an Fc-enhanced anti-B7-H3 monoclonal antibody with potent antitumor activity," *Clin. Cancer Res.*, 18(14):3834-3845 (2012).

Pardoll, "The blockade of immune checkpoints in cancer immunotherapy," *Nat. Rev. Cancer*, 12(4):252-264 (2012).

Parkin et al., Global cancer statistics, *CA Cancer J Clin.*, 49(1):33-64 (1999).

Sakuishi et al., "Targeting Tim-3 and PD-1 pathways to reverse T cell exhaustion and restore anti-tumor immunity," *J. Exp. Med.*, 207(10):2187-2194 (2010).

Scott et al., "Downregulation of myeloma-induced ICOS-L and regulatory T cell genereation by lenalidomide and dexamethasone therapy," *Cell. Immunol.*, 297(1):1-9 (2015).

Thompson et al., "Tumor B7-H1 is associated with poor prognosis in renal cell carcinoma patients with long-term follow-up," *Cancer Res.*, 66(7):3381-3385 (2006).

Tsushima et al., "Interaction between B7-H1 and PD-1 determines initiation and reversal of T-cell anergy," *Blood*, 110(1):180-185 (2007).

Wilen et al., "Strategies in optical resolutions," *Tetrahedron*, 33:2725-2736 (1977).

Wilen, Tables of Resolving Agents and Optical Resolutions, (E.L. Eliel, Ed.), University of Notre Dame Press, Notre Dame, IN, p. 268 (1972).

Wolchok et al., "Immune regulatory antibodies: are they the next advance," *Cancer J.*, 16(4):311-317 (2010).

Wolchok et al., "The mechanism of anti-CTLA-4 activity and the negative regulation of T-cell activation," *Oncologist*, 13(Supp 4):2-9 (2008).

* cited by examiner

COMBINATION THERAPY FOR TREATMENT OF HEMATOLOGICAL CANCERS AND SOLID TUMORS

This application claims is a U.S. National Stage filing under 35 U.S.C. § 371 of International Application No. PCT/US16/40718, filed Jul. 1, 2016, which claims the benefit of priority to U.S. Provisional Application Nos. 62/188,404, filed Jul. 2, 2015; 62/245,916, filed Oct. 23, 2015; 62/308,055, filed Mar. 14, 2016; and 62/340,972, filed May 24, 2016, the entireties of each of which are incorporated herein by reference.

1. FIELD

Provided herein are methods for treating, preventing and/or managing hematological cancers and solid tumors using combination therapies that include 3-(5-amino-2-methyl-4-oxo-4H-quinazolin-3-yl)-piperidine-2,6-dione and at least one checkpoint inhibitor.

2. BACKGROUND

Cancer can induce significant suppression of the immune system and escape from the immune surveillance mechanisms of the host. Dysregulation of host immune system is now considered one important hallmark of cancer (Hanahan et al., *Cell*, 2011, 144, 646-674). The interactions between cancer and the host immune system have been extensively studied and many types of immunotherapies have been explored for cancer treatment.

One class of immunotherapy is agents targeting specific checkpoint proteins that play critical roles in regulating T cell activation and proliferation. These proteins function as co-receptors on the surfaces of T cells and help regulate T cell responses following T cell activation (Wolchok et al., *Cancer* 1, 2010, 16, 311-317). The two best characterized checkpoint proteins are cytotoxic T-lymphocyte antigen 4 (CTLA-4) and programmed death-1 (PD-1), both serve as negative regulators of T cell activation. T cell activation induces expression of CTLA-4 on T lymphocytes, thereby inhibits further T cell activation and proliferation. Furthermore, anti-CTLA-4 antibodies can directly activate CD4(+) and CD8(+) effector cells and generate anti-tumor responses (Wolchok et al., *Oncologist*, 2008, 13 (suppl 4), 2-9). Pre-clinical models showed anti-tumor activity of anti-CTLA-4 antibodies in many tumor types, and a phase III randomized trial has demonstrated overall survival benefit of the anti-CTLA-4 antibody ipilimumab in patients with advanced melanoma (Hodi et al., *N. Engl. J. Med.*, 2010, 363, 711-723). PD-1 signaling plays an important role in promoting regulatory T cell (Treg) function and preventing auto-immunity (Francisco et al., *Immunol. Rev.*, 2010, 236, 219-242). Over-expression of PD-1 and its ligands, PD-L1 and PD-L2, has been found in many types of cancers and the over-expression was associated with advanced tumor stage and poor survival (Thompson et al., *Cancer Res.*, 2006, 66, 3381-3385; Hamanishi et al., *Proc. Natl. Acad. Sci. USA*, 2007, 104, 3360-3365). Blocking of PD-1/PD-1 ligand interaction by antibodies can inhibit Treg function, promote host immune response, and inhibit tumor growth in various cancer models (Tsushima et al., *Blood*, 2007, 110, 180-185; Iwai et al., *Proc. Natl. Acad. Sci. USA*, 2002, 99, 12293-12997). Early-phase clinical trials of anti-PD-1 antibodies have shown promising anti-tumor activity in solid cancers and hematological malignancies (Berger et al., *Clin. Cancer Res.*, 2008, 14, 3044-3051; Ansell et al., *N. Engl. J. Med.*, 2015, 372, 311-319).

A blood cancer or hematological malignancy is a type of malignant cancer that originates, affects, or involves the blood, bone marrow, or lymph nodes. These cancers include leukemias, lymphomas, and myelomas. These particular types of cancers can arise as defected mature cell types that have differentiated from hematopoietic precursor cells (often in the bone marrow) and begin to quickly proliferate through the bloodstream where it can then often infiltrate other organs and tissues. Others can involve the formation of tumors from lymphoblasts from within the lymphoid tissue.

The pathogenesis of lymphomas involves the accumulation of multiple genetic lesions affecting proto-oncogenes and tumor suppressor genes. The lymph node microenvironment, which includes stromal cells, macrophages, regulatory T-cells, and the lymph node vasculature, has been implicated in the promotion of lymphomagenesis.

Hodgkin lymphoma (HL), formerly called Hodgkin's disease, arises from germinal center or post-germinal center B-cells. Hodgkin lymphoma has a unique cellular composition, containing a minority of neoplastic cells (Reed-Sternberg cells and their variants) in an inflammatory background. Hodgkin lymphoma is a B-cell lymphoma that accounts for approximately 10% of all lymphomas in economically advanced countries. This amounts to approximately 9,050 new cases and about 1,150 deaths due to HL in the US annually. The incidence in Europe is approximately 2.4 cases per 100,000 persons.

Non-Hodgkin lymphoma (NHL), which often refers to group of lymphomas except Hodgkin lymphoma, is more common than Hodgkin lymphoma. About 90% of lymphomas are non-Hodgkin lymphomas. Common subtypes of NHL include diffuse large B-cell lymphoma, follicular lymphoma, mantle cell lymphoma, Burkitt lymphoma, and others. In 2015, it is estimated that there will be 71,850 new cases of non-Hodgkin lymphoma and an estimated 19,790 people will die from this disease annually in the U.S.

Chronic lymphocytic leukemia (CLL) is the most common leukemia in North America and Europe with an incidence of 4.0 cases per 100,000 persons per year and has a median age of diagnosis of 72 years. It consists of an accumulation of mature B-cells typically cluttering in marrow, blood and lymphoid organs with a unique CD19+, CD5+, and CD23+ phenotype.

Acute lymphoblastic leukemia, also known as acute lymphocytic leukemia or acute lymphoid leukemia (ALL), is an acute form of leukemia. ALL is most common in childhood, with a peak incidence at 2-5 years of age and another peak in old age. About 6,000 cases are reported in the United States every year.

Acute myeloid leukemia (AML), also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age.

Chronic myelogenous (or myeloid or myelocytic) leukemia (CML) is a form of leukemia characterized by the increased and unregulated growth of predominantly myeloid cells in the bone marrow and the accumulation of these cells in the blood. In Western countries it accounts for 15-20% of all adult leukemias and 14% of leukemias overall (including the pediatric population).

Myelodysplastic syndromes (MDS) are hematological medical conditions with ineffective production of all blood cells. The overall incidence of MDS in the United States is estimated at close to four cases per 100,000 people, with as many as 20,000 to 30,000 people diagnosed annually. There are several different types of MDS which can be further classified as low risk MDS or high risk MDS—depending on the progression and severity of the disease. Treatment for MDS includes blood transfusion, growth factors, chemotherapy, and bone marrow transplant or stem cell transplant. Many treatments can place MDS in remission but treatment failure and possible recurrence of MDS exist with few options available following treatment.

Myeloproliferative disorders (MPD) are a group of diseases of the bone marrow in which excess cells are produced. They are related to, and may evolve into, myelodysplastic syndrome and acute myeloid leukemia.

A tumor, also known as a neoplasm, is an abnormal mass of tissue which may be solid or fluid-filled. A solid tumor is an abnormal mass of tissue that usually does not contain cysts or liquid areas. Solid tumors may be benign (not cancer), or malignant (cancer). Different types of solid tumors are named for the type of cells that form them. Examples of solid tumors include sarcomas and carcinomas.

Hepatocellular carcinoma (HCC), also known as malignant hepatoma, is the most common primary malignancy of the liver and accounts for 80-90% of primary liver tumors. HCC is one of the most common and devastating malignant diseases worldwide, responsible for more than 1 million deaths annually in the world (Parkin et al., *C A Cancer J. Clin.* 1999, 49, 33-64; Bruix et al., *Cancer Cell* 2004, 5, 215-219). Although various chemotherapy regimens are available, traditionally, chemotherapy is not considered an effective treatment option for HCC. Systemic chemotherapy response rates of 10% can be seen, with response rates up to 20% using intra-arterial chemotherapy.

Despite of the recent development of immunotherapies, there remains a high unmet medical need for effective treatment involving immunotherapies for hematological cancers and solid tumors (such as HCC) that reduce treatment failure and reduce or eliminate recurrence or development of resistance to anti-cancer agents.

3. SUMMARY

Provided herein are methods of treating, preventing, and/or managing hematological cancers and solid tumors comprising administering to a patient in need thereof a therapeutically effective amount of 3-(5-amino-2-methyl-4-oxo-4H-quinazolin-3-yl)-piperidine-2,6-dione ("Compound A") of following formula, or a pharmaceutically acceptable salt, solvate, stereoisomer, or isotopologue thereof,

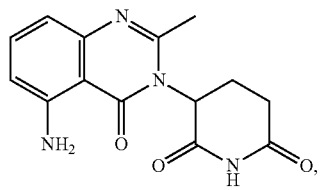 [SMILES: Cc1nc2cccc(N)c2c(=O)n1C1CCC(=O)NC1=O]

in combination with one or more checkpoint inhibitor(s). Compound A was described, e.g., in U.S. Pat. No. 7,635,700 and U.S. Publication No. 2012/0232100, isotopologues of Compound A were described, e.g., in International Application Publication No. WO 2014/039421 and U.S. Publication No. 2014/0228382, the disclosure of each of which is incorporated herein by reference in its entirety.

Also provided herein is a pharmaceutical compositions, dosage forms, dosing regimen, and kits that can be used in connection with the above-described methods.

4. DETAILED DESCRIPTION

4.1 Brief Description of Figures

4.2 Definitions

Figure 1:
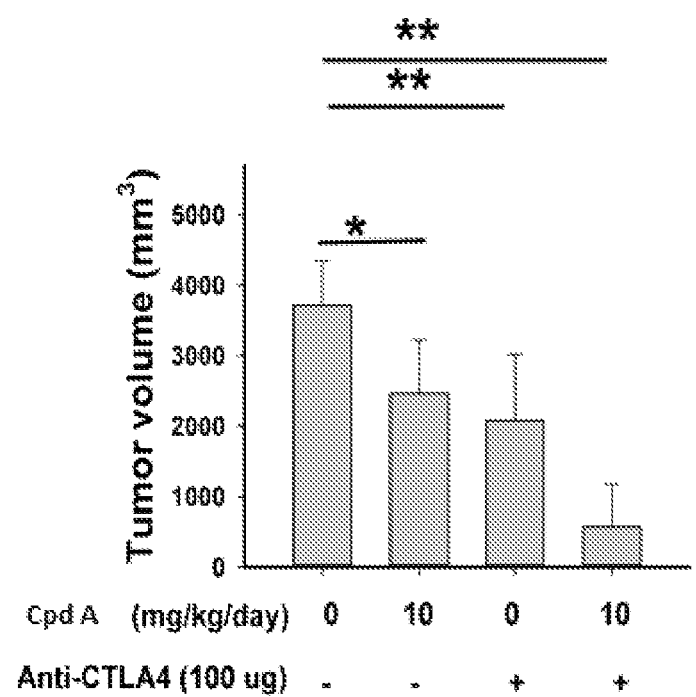
FIG. 1 shows the anti-tumor effects of combinations of Compound A with an anti-CTLA-4 antibody in an orthotopic liver cancer model.

All patents, applications, published applications and other publications are incorporated by reference in their entirety. The abbreviations used herein have their conventional meaning within the chemical and biological arts. The chemical structures and formulae set forth herein are constructed according to the standard rules of chemical valency known in the chemical arts. In the event that there is a plurality of definitions for a term herein, those in this section prevail unless stated otherwise. Headings used herein are for organizational purposes only and in no way limit the invention described herein.

As used herein, "administer" or "administration" refers to the act physically delivering a substance as it exists outside the body into a patient, such as by oral, mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

As used herein, the terms "subject" and "patient" are used interchangeably. As used herein, a subject can be a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a disease, disorder or condition described herein. In another embodiment, the subject is a mammal (e.g., a human) at risk of developing a disease, disorder or condition described herein.

The terms "cancer" and "cancerous" refer to or describe the physiological condition in mammals that is typically characterized by unregulated cell growth.

Hematological cancer as used herein refers to blood-borne tumors (e.g., multiple myeloma, lymphoma, and leukemia).

"Tumor" and "solid tumor" as used herein, refer to all lesions and neoplastic cell growth and proliferation, whether malignant or benign, and all pre-cancerous and cancerous cells and tissues. Other exemplary cancers are provided elsewhere herein. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

A "sarcoma" is a solid tumor which is made up of a substance like the embryonic connective tissue and is generally composed of closely packed cells embedded in a fibrillar or homogeneous substance. Exemplary sarcomas that can be treated, prevented, and/or managed using the compositions and methods described herein include chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

A "carcinoma" refers to a malignant new growth made up of epithelial cells tending to infiltrate the surrounding tissues and give rise to metastases. Exemplary carcinomas that can be treated with the compositions and methods described herein include, adenocarcimonas, colorectal carcinoma, colorectal adenocarcinoma, acinar carcinoma, lung carcinoma, alveolar cell carcinoma, basal cell carcinoma, bronchioalveolar carcinoma, bronchiolar carcinoma, bronchogenic carcinoma, cerebriform carcinoma, chorionic carcinoma, colloid carcinoma, corpus carcinoma, cribriform carcinoma, cylindrical carcinoma, cylindrical cell carcinoma, duct carcinoma, gelatiniforni carcinoma, gelatinous carcinoma, giant cell carcinoma, carcinoma gigantocellulare, glandular carcinoma, hematoid carcinoma, hepatocellular carcinoma, Hurthle cell carcinoma, Krompecher's carcinoma, Kulchitzky-cell carcinoma, large-cell carcinoma, lymphoepithelial carcinoma, nasopharyngeal carcinoma, papillary carcinoma, renal cell carcinoma of kidney, scirrhous carcinoma, small-cell carcinoma, spheroidal cell carcinoma, squamous carcinoma, squamous cell carcinoma, carcinoma telangiectaticum, and verrucous carcinoma.

As used herein, unless otherwise specified, the term "treat," "treating," or "treatment" refers to alleviating or abrogating a disease, or one or more of the symptoms associated with the disease; or alleviating or eradicating the cause(s) of the disease itself. "Treat," "treatment" and "treating" also refer to the reduction or amelioration of the progression, severity, and/or duration of a disease, disorder or condition described herein resulting from the administration of one or more therapies.

As used herein, unless otherwise specified, the term "preventing" refers to the treatment with or administration of a compound provided herein, with or without other additional active compound, prior to the onset of symptoms, particularly to patients at risk of cancer and/or other disorders described herein. The term "prevention" includes the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. In certain cases, the beneficial effects that a subject derives from a prophylactic or therapeutic agent do not result in a cure of the disease or disorder. In certain embodiments, a subject is administered one or more therapies to "manage" a disease, disorder or condition, or one or more symptoms thereof, so as to prevent the progression or worsening of the disease, disorder or condition.

As used herein, unless otherwise specified, the term "therapeutically effective amount" of a compound refers to the amount of a compound that, when administered, is sufficient to prevent development of, or alleviate to some extent, one or more of the symptoms of a disease being treated. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. Furthermore, a therapeutically effective amount of a compound means an amount of a therapeutic agent, alone or in combination with other therapies, which provides a therapeutic benefit in the treatment or management of a disease. The term encompasses an amount that improves overall therapy, reduces, or avoids symptoms or causes of a disease, or enhances the therapeutic efficacy of another therapeutic agent.

As used herein, and unless otherwise specified, a "prophylactically effective amount" of a compound is an amount sufficient to inhibit or reduce a symptom of a disease or to prevent recurrence of a disease. A prophylactically effective amount of a compound means an amount of therapeutic agent, alone or in combination with other agents, which provides a prophylactic benefit in the inhibition or reduction of a symptom of a disease or recurrence of a disease. The term "prophylactically effective amount" can encompass an amount that improves overall prophylaxis or enhances the prophylactic efficacy of another prophylactic agent.

As used herein, the term "therapy" refers to any protocol, method and/or agent that can be used in the prevention, management, treatment and/or amelioration of a given disease, disorder or condition. In certain embodiments, the terms "therapies" and "therapy" refer to a drug therapy, biological therapy, supportive therapy, and/or other therapies useful in the prevention, management, treatment and/or amelioration of a given disease, disorder or condition known to one of skill in the art such as medical personnel.

As used herein, and unless otherwise specified, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucuronic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In one embodiment, suitable are hydrochloric, hydrobromic, phosphoric, and sulfuric acids.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, greater than about 98% by weight of one stereoisomer of the compound and less than about 2% by weight of the other stereoisomers of the compound or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

As used herein, unless otherwise specified, the terms "antibody" means a polypeptide product of B cells within the immunoglobulin class of polypeptides that is able to bind to a specific molecular antigen. Antibodies provided herein include, but are not limited to, monoclonal antibodies, bispecific antibodies, minibodies, domain antibodies, synthetic antibodies, antibody mimetics, chimeric antibodies, humanized antibodies, human antibodies, antibody fusions, antibody conjugates, single chain antibodies, antibody derivatives, antibody analogues and fragments thereof, respectively. Also included are immunological fragments of an antibody (e.g., a Fab, a Fab', a F(ab')$_2$, or a scFv), irrespective of whether such antibodies are produced, in whole or in part, via immunization, through recombinant technology, by way of in vitro synthetic means, or otherwise.

As used herein, unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning; A Laboratory Manual* (2d ed.); D. N Glover, ed. (1985) *DNA Cloning*, Volumes I and II; M. J. Gait, ed. (1984) *Oligonucleotide Synthesis*; B. D. Hames & S J. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

4.3 Compounds 4.3.1 Compound A

In some embodiments, the compound suitable for use in the methods provided herein is 3-(5-amino-2-methyl-4-oxo-4H-quinazolin-3-yl)-piperidine-2,6-dione (Compound A) having the structure of the following formula:

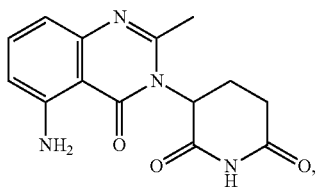 [SMILES: Cc1nc2cccc(N)c2c(=O)n1C1CCC(=O)NC1=O]

or an enantiomer or a mixture of enantiomers thereof or a pharmaceutically acceptable salt, solvate, hydrate, co-crystal, clathrate, polymorph, or isotopologue thereof.

Compound A can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein.

Compound A markedly inhibits TNF-α, IL-1β, and other inflammatory cytokines in LPS-stimulated hPBMC and human whole blood. TNF-α is an inflammatory cytokine produced by macrophages and monocytes during acute inflammation. TNF-α is responsible for a diverse range of signaling events within cells. TNF-α may play a pathological role in cancer. Without being limited by theory, one of the biological effects exerted by Compound A is the reduction of synthesis of TNF-α. Compound A enhances the degradation of TNF-α mRNA. Compound A also potently inhibits IL-1β and stimulates IL-10 under these conditions.

Further, without being limited by theory, Compound A is a potent co-stimulator of T cells and increase cell proliferation in a dose dependent manner under appropriate conditions.

In certain embodiments, without being limited by theory, the biological effects exerted by Compound A include, but not limited to, anti-angiogenic and immune modulating effects.

In certain embodiments, Compound A is a solid. In certain embodiments, Compound A is hydrated. In certain embodiments, Compound A is solvated. In certain embodiments, Compound A is anhydrous. In certain embodiments, Compound A is nonhygroscopic.

In certain embodiments, Compound A is amorphous. In certain embodiments, Compound A is crystalline. In certain embodiments, Compound A is in a crystalline form described in U.S. Publication No. 2012/0232100-A1, which is incorporated herein by reference in its entirety.

The solid forms of Compound A can be prepared according to the methods described in the disclosure of U.S. Publication No. 2012/0232100-A1. The solid forms can be also prepared according to other methods apparent to those of skill in the art.

In certain embodiments, Compound A is a hydrochloride salt of 3-(5-amino-2-methyl-4-oxo-4H-quinazolin-3-yl)-piperidine-2,6-dione, or an enantiomer or a mixture of enantiomers thereof; or a pharmaceutically acceptable solvate, hydrate, co-crystal, clathrate, or polymorph thereof. In certain embodiments, the hydrochloride salt is a solid. In certain embodiments, the hydrochloride salt is anhydrous. In certain embodiments, the hydrochloride salt is nonhygroscopic. In certain embodiments, the hydrochloride salt is amorphous. In certain embodiments, the hydrochloride salt is crystalline. In certain embodiments, the hydrochloride salt is in crystalline Form A.

The hydrochloride salt of Compound A and solid forms thereof can be prepared according to the methods described in the disclosure of U.S. Publication No. 2012/0232100-A1. The hydrochloride salt the solid forms thereof can be also prepared according to other methods apparent to those of skill in the art.

Compound A provided herein contains one chiral center, and can exist as a mixture of enantiomers, e.g., a racemic mixture. This disclosure encompasses the use of stereomerically pure forms of such a compound, as well as the use of mixtures of those forms. For example, mixtures comprising equal or unequal amounts of the enantiomers of Compound A provided herein may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

In some embodiment, an isotopologue of Compound A is administered in the methods provided herein. Compound A can contain unnatural proportions of atomic isotopes at one or more of the atoms. For example, the compound may be radiolabeled with radioactive isotopes, such as for example tritium (3H), iodine-125 (125I), sulfur 35 (35S), or carbon-14 (14C), or may be isotopically enriched, such as with deuterium (2H), carbon-13 (13C), or nitrogen-15 (15N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, research reagents, e.g., binding assay reagents, and diagnostic agents, e.g., in vivo imaging agents. All isotopic variations of Compound A, whether radioactive or not, are intended to be encompassed within the scope of the embodiments provided herein. In some embodiments, provided herein are isotopologues of Compound A, for example, the isotopologues are deuterium, carbon-13, or nitrogen-15 enriched Compound A. In some embodiments, provided herein are deuterium isotopologues of Compound A. One or more or all of the hydrogen atoms in Compound A can be isotopically enriched with deuterium. Specific isotopologues of Compound A include those described, e.g., in International Application Publication No. WO 2014/039421 and U.S. Publication No. 2014/0228382.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

4.3.2 Checkpoint Inhibitors (CPI)

In some embodiments, one or more checkpoint inhibitor(s) are used in combination with Compound A in connection with methods provided herein. In one embodiment, one checkpoint inhibitor is used in combination with Compound A in connection with methods provided herein. In another embodiment, two checkpoint inhibitors are used in combination with Compound A in connection with methods provided herein. In yet another embodiment, three or more checkpoint inhibitors are used in combination with Compound A in connection with methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer*, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.*, 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.*, 2012, 3834).

In one embodiment, the checkpoint inhibitors is a TIM3 (T-cell immunoglobulin domain and mucin domain 3) inhibitor (Fourcade et al., *J. Exp. Med.*, 2010, 207, 2175-86; Sakuishi et al., *J. Exp. Med.*, 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with secondary active agents as described herein where appropriate for treating diseases described herein and understood in the art.

4.4 Methods of Treatment, Prevention and/or Management

Provided herein are methods of treating, preventing, and/or managing hematological cancers or solid tumors comprising administering to a subject in need thereof a combination therapy described herein. In one aspect is a method of treating hematological cancers or solid tumors comprising administering to a subject in need thereof a combination therapy described herein. In another aspect is a method of preventing hematological cancers or solid tumors comprising administering to a subject in need thereof a combination therapy described herein. In still another aspect is a method of managing hematological cancers or solid tumors comprising administering to a subject in need thereof a combination therapy described herein.

In one embodiment, provided herein is a method of treating, preventing, or managing a hematological cancer or solid tumor comprising administering to a patient in need thereof a therapeutically or prophylactically effective amount of Compound A of following formula, or a pharmaceutically acceptable salt, solvate, stereoisomer, or isotopologue thereof:

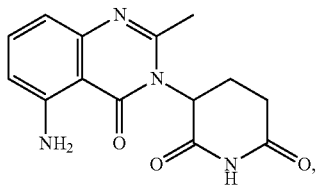 [SMILES: Cc1nc2cccc(N)c2c(=O)n1C1CCC(=O)NC1=O]

in combination with a therapeutically or prophylactically effective amount of one or more checkpoint inhibitor(s). In one embodiment, provided herein is a method of treating a hematological cancer or solid tumor comprising administering to a patient in need thereof a therapeutically effective amount of Compound A, or a pharmaceutically acceptable salt, solvate, stereoisomer, or isotopologue thereof, in combination with a therapeutically effective amount of a checkpoint inhibitor.

In one embodiment, the checkpoint inhibitor is a CTLA-4 inhibitor. In one embodiment, wherein the CTLA-4 inhibitor is an anti-CTLA-4 antibody. In one embodiment, the anti-CTLA-4 antibody is tremelimumab or ipilimumab. In one embodiment, the anti-CTLA-4 antibody is tremelimumab. In another embodiment, the anti-CTLA-4 antibody is ipilimumab.

In one embodiment, provided herein is a method of treating or managing a hematological cancer or solid tumor comprising administering to a patient in need thereof a therapeutically effective amount of Compound A, or a pharmaceutically acceptable salt, solvate, stereoisomer, or isotopologue thereof, in combination with a therapeutically effective amount of tremelimumab.

In one embodiment, provided herein is a method of treating or managing a hematological cancer or solid tumor comprising administering to a patient in need thereof a therapeutically effective amount of Compound A, or a pharmaceutically acceptable salt, solvate, stereoisomer, or isotopologue thereof, in combination with a therapeutically effective amount of ipilimumab.

In one embodiment, the checkpoint inhibitor is a PD-1 inhibitor. In one embodiment, the PD-1 inhibitor is an anti-PD-1 antibody. In one embodiment, the anti-PD-1 antibody is nivolumab, pembrolizumab, or pidilizumab. In one embodiment, the anti-PD-1 antibody is nivolumab. In another embodiment, the anti-PD-1 antibody is pembrolizumab. In yet another embodiment, the anti-PD-1 antibody is pidilizumab.

In one embodiment, provided herein is a method of treating or managing a hematological cancer or solid tumor comprising administering to a patient in need thereof a therapeutically or prophylactically effective amount of Compound A, or a pharmaceutically acceptable salt, solvate, stereoisomer, or isotopologue thereof, in combination with a therapeutically or prophylactically effective amount of nivolumab.

In one embodiment, provided herein is a method of treating or managing a hematological cancer or solid tumor comprising administering to a patient in need thereof a therapeutically or prophylactically effective amount of Compound A, or a pharmaceutically acceptable salt, solvate, stereoisomer, or isotopologue thereof, in combination with a therapeutically or prophylactically effective amount of pembrolizumab.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736. In another embodiment, the anti-PD-L1 antibody is MPDL3280A (also known as atezolizumab).

In one embodiment, provided herein is a method of treating or managing a hematological cancer or solid tumor comprising administering to a patient in need thereof a therapeutically or prophylactically effective amount of Compound A, or a pharmaceutically acceptable salt, solvate, stereoisomer, or isotopologue thereof, in combination with a therapeutically or prophylactically effective amount of MEDI4736.

In one embodiment, Compound A, or a pharmaceutically acceptable salt, solvate, stereoisomer, or isotopologue thereof, is administered in combination with two checkpoint inhibitors. In one embodiment, Compound A, or a pharmaceutically acceptable salt, solvate, stereoisomer, or isotopologue thereof, is administered in combination with two checkpoint inhibitors independently selected from an anti-CTLA-4 antibody, an anti-PD-1 antibody, and an anti-PD-L1 antibody. In one embodiment, Compound A, or a pharmaceutically acceptable salt, solvate, stereoisomer, or isotopologue thereof, is administered in combination with an anti-CTLA-4 antibody and an anti-PD-1 antibody. In another embodiment, Compound A, or a pharmaceutically acceptable salt, solvate, stereoisomer, or isotopologue thereof, is administered in combination with an anti-CTLA-4 antibody and an anti-PD-L1 antibody. In one embodiment, the anti-CTLA-4 antibody is tremelimumab or ipilimumab. In one embodiment, the anti-PD-1 antibody is nivolumab, pembrolizumab, or pidilizumab. In one embodiment, the anti-PD-L1 antibody is MEDI4736 or MPDL3280A.

Patients benefitting from the methods described herein can include patients who have been previously treated for cancer but are non-responsive to standard therapies. In such instances patients may be non-responsive or have developed resistance to anti-cancer treatments. Patients may have cancer refractory or otherwise non-response to at least one anticancer therapy. Patients may also include patients who have not previously been treated by administering a combination therapy as described herein. Patients can also include those patients who have undergone surgery in an attempt to treat the disease or condition at issue. The methods and combination therapies described herein are also applicable to patients who have not undergone surgery prior to administration. Patients currently taking agents for treating cancer (e.g., concurrently chemotherapy, immunotherapy, biologics, or hormonal therapy), in certain instances, may be excluded from the methods described herein.

In one embodiment, the methods described herein are useful for treating, preventing, and/or managing cancer of the skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. In one embodiment, cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, follicular lymphoma, low grade follicular lymphoma, acute myelogenous leukemia, acute lymphocytic leukemia, chronic myelogenous leukemia, chronic lymphocytic leukemia, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, provided herein is a method of treating or managing a hematological cancer comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). The combination therapy can include secondary active agents as described herein. In certain embodiments, the hematological cancer is myeloma, lymphoma or leukemia. In certain embodiments, the hematological cancer is myeloma. In certain embodiments, the hematological cancer is lymphoma. In certain embodiments, the hematological cancer is leukemia.

In one embodiment, the hematological cancer is multiple myeloma (MM). In one embodiment, the hematological cancer is relapsed/refractory (R/R) multiple myeloma. In one embodiment, the patient having R/R multiple myeloma has impaired renal function. In one embodiment, the hematological cancer is newly diagnosed multiple myeloma. In one embodiment, the hematological cancer is smoldering multiple myeloma.

In one embodiment, the hematological cancer is acute myeloid leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CIVIL), myelodysplastic syndrome (MDS), human lymphotropic virus-type 1 (HTLV-1) leukemia, mastocytosis, or B-cell acute lymphoblastic leukemia. In one embodiment, the hematological cancer is CLL. In one embodiment, the hematological cancer is AML. In one embodiment, the hematological cancer is ALL. In one embodiment, the hematological cancer is MDS. In one embodiment, the hematological cancer is adult T-cell leukemia.

In one embodiment, the hematological cancer is diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma (PMBCL), splenic marginal zone lymphoma, Richter's transformation, primary CNS lymphoma (PCNSL), cutaneous T-cell lymphoma (CTCL), peripheral T-cell Lymphoma (PTCL), NK/T-cell lymphoma (e.g., nasal type), Waldenstrom macroglobulinemia (WM), plasmacytoma, cutaneous B-cell lymphoma (CBCL), nodal marginal zone lymphoma, or ALK-positive large B-cell lymphoma. In one embodiment, the hematological cancer is HL. In one embodiment, the hematological cancer is NHL. In one embodiment, the hematological cancer is indolent lymphoma including, for example, DLBCL, follicular lymphoma, or marginal zone lymphoma (MZL). In one embodiment, the hematological cancer is Richter's transformation. In one embodiment, the hematological cancer is primary CNS lymphoma (PCNSL). In one embodiment, the hematological cancer is primary mediastinal large B-cell lymphoma (PMBCL). In one embodiment, the hematological cancer is peripheral T-cell Lymphoma (PTCL). In one embodiment, the hematological cancer is NK/T-cell lymphoma. In one embodiment, the NK/T-cell lymphoma is nasal type. In one embodiment, the hematological cancer is adult T-cell lymphoma.

In certain embodiments, the hematological cancer is drug resistant to at least one anticancer therapy. In certain embodiments the hematological cancer is relapsed or refractory to at least one anticancer therapy. In certain embodiments the hematological cancer is relapsed or refractory to two prior anticancer therapies (e.g., double refractory). In certain embodiments, the hematological cancer is metastatic.

In one embodiment, provided herein is a method of treating or managing a lymphoma comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, the lymphoma is a B-cell lymphoma. In one embodiment, the lymphoma is a T-cell lymphoma.

In one embodiment, provided herein is a method of treating or managing Hodgkin lymphoma (HL) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing HL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating HL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months).

In one embodiment, provided herein is a method of treating HL comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months).

In one embodiment, provided herein is a method of treating or managing non-Hodgkin's lymphoma (NHL) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the NHL is an aggressive NHL. In one embodiment, the NHL is an indolent NHL. In one embodiment, the NHL is cutaneous T cell lymphoma (CTCL), peripheral T-cell Lymphoma (PTCL), follicular lymphoma (FL), mantle cell lymphoma (MCL), Waldenstrom macroglobulinemia (WM), or plasmacytoma.

In one embodiment, provided herein is a method of treating or managing NHL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the NHL is an aggressive NHL. In one embodiment, the NHL is an indolent NHL. In one embodiment, the NHL is cutaneous T cell lymphoma (CTCL), peripheral T-cell Lymphoma (PTCL), follicular lymphoma (FL), mantle cell lymphoma (MCL), Waldenstrom macroglobulinemia (WM), or plasmacytoma.

In one embodiment, provided herein is a method of treating NHL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months). In one embodiment, the NHL is an aggressive NHL. In one embodiment, the NHL is an indolent NHL. In one embodiment, the NHL is cutaneous T cell lymphoma (CTCL), peripheral T-cell Lymphoma (PTCL), follicular lymphoma (FL), mantle cell lymphoma (MCL), Waldenstrom macroglobulinemia (WM), or plasmacytoma.

In one embodiment, provided herein is a method of treating NHL comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months). In one embodiment, the NHL is an aggressive NHL. In one embodiment, the NHL is an indolent NHL. In one embodiment, the NHL is cutaneous T cell lymphoma (CTCL), peripheral T-cell Lymphoma (PTCL), follicular lymphoma (FL), mantle cell lymphoma (MCL), Waldenstrom macroglobulinemia (WM), or plasmacytoma.

In one embodiment, provided herein is a method of treating or managing diffuse large B-cell lymphoma (DLBCL) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing DLBCL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating DLBCL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months).

In one embodiment, provided herein is a method of treating DLBCL comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months).

In one embodiment, provided herein is a method of treating or managing follicular lymphoma (FL) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the FL is relapsed or refractory. In one embodiment, the FL is refractory to one, two, or more prior therapies. In one embodiment, the FL is refractory to two prior therapies (e.g., double refractory FL). In one embodiment, the FL is refractory to an anti-CD20 therapy and a chemotherapy. In one embodiment, the anti-CD20 therapy is rituximab. In one embodiment, the chemotherapy is an alkylating agent.

In one embodiment, provided herein is a method of treating or managing FL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the FL is relapsed or refractory. In one embodiment, the FL is refractory to one, two, or more prior therapies. In one embodiment, the FL is refractory to two prior therapies (e.g., double refractory FL). In one embodiment, the FL is refractory to an anti-CD20 therapy and a chemotherapy. In one embodiment, the anti-CD20 therapy is rituximab. In one embodiment, the chemotherapy is an alkylating agent.

In one embodiment, provided herein is a method of treating FL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months). In one embodiment, the FL is relapsed or refractory. In one embodiment, the FL is refractory to one, two, or more prior therapies. In one embodiment, the FL is refractory to two prior therapies (e.g., double refractory FL). In one embodiment, the FL is refractory to an anti-CD20 therapy and a chemotherapy. In one embodiment, the anti-CD20 therapy is rituximab. In one embodiment, the chemotherapy is an alkylating agent.

In one embodiment, provided herein is a method of treating FL comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months). In one embodiment, the FL is relapsed or refractory. In one embodiment, the FL is refractory to one, two, or more prior therapies. In one embodiment, the FL is refractory to two prior therapies (e.g., double refractory FL). In one embodiment, the FL is refractory to an anti-CD20 therapy and a chemotherapy. In one embodiment, the anti-CD20 therapy is rituximab. In one embodiment, the chemotherapy is an alkylating agent.

In one embodiment, provided herein is a method of treating or managing mantle cell lymphoma (MCL) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing MCL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating MCL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months).

In one embodiment, provided herein is a method of treating MCL comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months).

In one embodiment, provided herein is a method of treating or managing a myeloma comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s).

In one embodiment, provided herein is a method of treating or managing multiple myeloma (e.g., relapsed multiple myeloma, refractory multiple myeloma, smoldering multiple myeloma, and newly diagnosed multiple myeloma) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, the multiple myeloma is relapsed or refractory multiple myeloma. In one embodiment, the multiple myeloma is smoldering multiple myeloma. In one embodiment, the multiple myeloma is newly diagnosed multiple myeloma.

In one embodiment, provided herein is a method of treating or managing multiple myeloma (e.g., relapsed multiple myeloma, refractory multiple myeloma, smoldering multiple myeloma, and newly diagnosed multiple myeloma) comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the multiple myeloma is relapsed or refractory multiple myeloma. In one embodiment, the multiple myeloma is smoldering multiple myeloma. In one embodiment, the multiple myeloma is newly diagnosed multiple myeloma.

In one embodiment, provided herein is a method of treating multiple myeloma (e.g., relapsed multiple myeloma, refractory multiple myeloma, smoldering multiple myeloma, and newly diagnosed multiple myeloma) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In one embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months). In one embodiment, the multiple myeloma is relapsed or refractory multiple myeloma. In one embodiment, the multiple myeloma is smoldering multiple myeloma. In one embodiment, the multiple myeloma is newly diagnosed multiple myeloma.

In one embodiment, provided herein is a method of treating multiple myeloma (e.g., relapsed multiple myeloma, refractory multiple myeloma, smoldering multiple myeloma, and newly diagnosed multiple myeloma) comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months). In one embodiment, the multiple myeloma is relapsed or refractory multiple myeloma. In one embodiment, the multiple myeloma is smoldering multiple myeloma. In one embodiment, the multiple myeloma is newly diagnosed multiple myeloma.

In one embodiment, provided herein is a method of treating or managing a leukemia comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s).

In one embodiment, provided herein is a method of treating or managing a myelodysplastic syndrome (MDS) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). The MDS can be a low risk MDS (LR MDS). The MDS can be a high risk MDS (HR MDS). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In one embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the MDS is resistant to treatment with hypomethylating agents (HMAs). In one embodiment the MDS is developed from a treatment with a therapy (tMDS), e.g., therapy induced.

In one embodiment, provided herein is a method of treating or managing MDS comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating MDS comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months).

In one embodiment, provided herein is a method of treating MDS comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months).

In one embodiment, provided herein is a method of treating or managing AML comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, the AML is R/R AML, trilineage dysplasia AML (AML-TLD), or therapy induced AML (tAML). In one embodiment, the patient has undergone treatment with a HMA. In one embodiment, the patient has HMA refractory AML. In one embodiment, the patient has not received a prior therapy for the AML, i.e., the method provided herein is the first line treatment for the AML.

In one embodiment, provided herein is a method of treating or managing AML comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months).

In one embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the AML, is relapsed or refractory. In one embodiment, the patient has not received a prior therapy for the AML.

In one embodiment, provided herein is a method of treating or managing AML comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months). In one embodiment, the AML is relapsed or refractory. In one embodiment, the patient has not received a prior therapy for the AML.

In one embodiment, provided herein is a method of treating AML comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months). In one embodiment, the AML is relapsed or refractory. In one embodiment, the patient has not received a prior therapy for the AML.

In one embodiment, provided herein is a method of treating AML comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months). In one embodiment, the AML is relapsed or refractory. In one embodiment, the patient has not received a prior therapy for the AML.

In one embodiment, provided herein is a method of treating or managing CIVIL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, the CML is R/R CML. In one embodiment, a combination therapy described herein is administered in combination with a secondary active agent. The secondary active agent can be an anti-cancer agent as described herein. In one embodiment, the secondary active agent is a tyrosine kinase inhibitor (TKI).

In one embodiment, provided herein is a method of treating or managing CIVIL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In one embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing CIVIL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating CML comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months).

In one embodiment, provided herein is a method of treating CML comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months).

In one embodiment, provided herein is a method of treating or managing ALL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, the ALL is R/R ALL.

In one embodiment, provided herein is a method of treating or managing ALL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In one embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing ALL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating ALL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months).

In one embodiment, provided herein is a method of treating ALL comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months).

In one embodiment, provided herein is a method of treating or managing CLL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, the CLL is R/R CLL.

In one embodiment, provided herein is a method of treating or managing CLL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In one embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing CLL comprising administering to a patient in need thereof a therapeutically effective amount of Compound A, or a pharmaceutically acceptable salt, solvate, stereoisomer, or isotopologue thereof, in combination with a therapeutically effective amount of durvalumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and durvalumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and durvalumab is administered at an amount and frequency as described herein (e.g., weekly in a 7 day cycle) prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating CLL comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a secondary active agent. In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; the CPI is administered prior to, concomitantly with, or subsequent to administration of Compound A on one or more days (e.g., on day 1 of cycle 1), and the secondary agent is administered weekly. In one embodiment, the combination therapy is administered for 1 to 13 cycles of 7 days (e.g., about 3 months).

In one embodiment, provided herein is a method of treating CLL comprising administering to a patient in need thereof a therapeutically effective amount of Compound A, or a pharmaceutically acceptable salt, solvate, stereoisomer, or isotopologue thereof, in combination with a therapeutically effective amount of durvalumab and rituximab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); durvalumab is administered at an amount and frequency as described herein (e.g., monthly in a 28 day cycle) prior to, concomitantly with, or subsequent to administration of Compound A on one or more days (e.g., on day 1 of cycle 1) and rituximab is administered in an amount and frequency as described herein (e.g., weekly). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); durvalumab is administered at an amount and frequency as described herein (e.g., weekly in a 7 day cycle) prior to, concomitantly with, or subsequent to administration of Compound A on one or more days (e.g., on day 1 of cycle 1) and rituximab is administered in an amount and frequency as described herein (e.g., weekly). In one embodiment, the combination therapy is administered for 1 to 13 cycles of 7 days (e.g., about 3 months).

In one embodiment, provided herein is a method of treating or managing a myeloproliferative disorder (MPD) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s).

Further provided herein are methods for treating myelofibrosis using a combination therapy described herein.

In certain embodiments, administration of a combination therapy as described herein modulates expression levels of at least one checkpoint proteins described herein (e.g., PD-L1). Thus, provided herein are methods of determining the expression of at least of checkpoint proteins, where the determination of the expression level is performed before, during, and/or after administration of a combination therapy described herein. The checkpoint protein expression levels determined before, during, and/or after administration of a combination therapy as described herein can be compared against each other or standard controls. Such comparisons can translate into determination of the efficacy of the administered treatment where in one embodiment a level of decreased expression of a given checkpoint protein indicates a greater effectiveness of the combination therapy.

In certain instances the combination therapies described herein reduce or eliminate minimal residual disease (MRD) state of a cancer (e.g., a hematological cancer (e.g., a lymphoma or leukemia), a sarcoma) described herein. In one embodiment, a combination therapy described herein is administered to a patient in need thereof, wherein said administration reduces or eliminates MRD. In one embodiment, the combination therapy is administered after administration of chemotherapy. In another embodiment, the combination therapy is administered during chemotherapy. In yet another embodiment, the combination therapy is administered as a chemotherapeutic therapy.

Also provided herein are methods where a combination therapy described herein is administered before or after a stem cell transplant (SCT) such as a bone marrow stem cell transplant (BMSCT). In certain instances, the level of expression of a checkpoint protein is determined for such stem cells pre- and post-transplant and pre- and post-administration with a combination therapy as described herein. In one embodiment, a combination therapy described herein is administered after a SCT (e.g., 1-24 hours, 1-3 days, 1-10 days, 1-3 months, 3-6 months, or 6-12 months post transplant). In another embodiment, a combination therapy described herein is administered within 180 days of a SCT. In certain embodiments administration of a combination therapy described herein reduces or eliminates development of graft v. host disease in a patient. In another embodiment administration of a combination therapy as described herein reduces or eliminates the need for immunosuppressive therapies following a SCT.

In another embodiment, administration of a combination therapy described herein is performed after a donor lymphocyte infusion (DLI). DLI can be used to stimulate a donor-versus-leukemia (GVL) reaction and thus eradicate the malignant clone of cells. DLI uses the collection (from the original donor) of peripheral lymphocytes during an apheresis procedure; donors generally undergo 2 to 8 procedures. The lymphocytes are then infused into the patient either immediately or after frozen storage. Donor lymphocyte infusion differs from allogeneic bone marrow transplantation in that it is not preceded by chemotherapy and T cells are not depleted. Lymphocyte infusion with a defined T-cell dose can cause a profound GVL effect and can be an effective form of salvage immunotherapy in allogeneic marrow transplanted recipients. In certain embodiments DLI lowers treatment-related morbidity and mortality when compared to second allogeneic transplantation.

In another embodiment, administration of a combination therapy described herein prolongs complete remission (CR) of a cancer (e.g., a hematological cancer (e.g., a lymphoma or leukemia), a sarcoma) after chemotherapy. CR can be prolonged by administering the combination therapies described herein (and optionally with co-administration of secondary active agents described herein) for hematological cancers including MDS, AML, ALL, CML, and CLL as described herein.

In certain embodiments, treatment using the combination therapies described herein can be monitored or determined using assays to determine expression levels of checkpoint proteins described herein (e.g., PD-L1, TIM-3, LAG-3, CTLA-4, OX40, Treg, CD25, CD127, FoxP3). Determining the expression of such checkpoint proteins can be performed before, during, or after completion of treatment with a combination therapy described herein. Expression can be determined using techniques known in the art, including for example flow-cytometry.

In certain embodiments, the MDS is drug resistant to at least one anticancer therapy. In certain embodiments, the MDS is refractory to at least one anticancer therapy.

In certain embodiments, a combination therapy as described herein is administered in combination with fludarabine, carboplatin, and/or topotecan to patients with refractory or relapsed or high-risk acute myelogenous leukemia.

In certain embodiments, a combination therapy as described herein is administered in combination with liposomal daunorubicin, topotecan and/or cytarabine to patients with unfavorable karotype acute myeloblastic leukemia.

In certain embodiments, provided herein is a method of treating or managing a solid tumor comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). The combination therapy can include secondary active agents as described herein. In one embodiment, the solid tumor is a carcinoma. In one embodiment, the solid tumor is a sarcoma. In one embodiment, the solid tumor is liver cancer, pancreatic cancer, renal cell cancer, lung cancer, skin cancer, thyroid cancer, brain tumor, colorectal cancer, bladder cancer, breast cancer, ovarian cancer, or head or neck cancer. In one embodiment, the solid tumor is glioma, glioblastoma, primary ductal carcinoma, lung carcinoma, colon adenocarcinoma, colorectal carcinoma, hepatocelluclar carcinoma, colorectal adenocarcinoma, amyloidosis, neuroendocrine tumors, Kaposi's sarcoma, non-small cell lung cancer, small cell lung cancer, melanoma (e.g., metastatic melanoma), soft tissue sarcoma, or scleroderma.

In certain embodiments, the solid tumor is drug resistant to at least one anticancer therapy. In certain embodiments the solid tumor is relapsed or refractory to at least one anticancer therapy. In certain embodiments, the solid tumor is metastatic.

In one embodiment, provided herein is a method of treating or managing hepatocellular carcinoma (HCC) comprising administering to a patient in need thereof a therapeutically effective amount of Compound A, or a pharmaceutically acceptable salt, solvate, stereoisomer, or isotopologue thereof, in combination with a therapeutically effective amount of a checkpoint inhibitor. In one embodiment, HCC is unresectable HCC. In one embodiment, the HCC is newly diagnosed, relapsed, refractory, or relapsed and refractory. In one embodiment, the patient has received no prior systemic therapy for HCC. In one embodiment, the patient has received prior therapy for HCC. In one embodiment, the patient has demonstrated progression or intolerance on the prior therapy. In one embodiment, the prior therapy is treatment with sorafenib.

In one embodiment, provided herein is a method of treating or managing HCC (e.g., unresectable HCC) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing HCC (e.g., unresectable HCC) comprising administering to a patient in need thereof a therapeutically effective amount of Compound A, or a pharmaceutically acceptable salt, solvate, stereoisomer, or isotopologue thereof, in combination with a therapeutically effective amount of nivolumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and nivolumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and nivolumab is administered at an amount and frequency as described herein (e.g., weekly in a 7 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered (e.g., orally) once daily for 5 consecutive days followed by 2 days of rest in one or more 7 days cycles; and nivolumab is administered (e.g., intravenously) once every 2 weeks. In another embodiment, Compound A, or a pharmaceutically acceptable salt, solvate, stereoisomer, or isotopologue thereof, is administered (e.g., orally) at a dose of about 2 mg once daily for 5 consecutive days followed by 2 days of rest in one or more 7 days cycles; and nivolumab is administered (e.g., intravenously) at a dose of about 3 mg/kg once every 2 weeks. In one embodiment, the combination therapy is administered for 1 to 13 cycles of 7 days (e.g., about 3 months).

In one embodiment, provided herein is a method of treating or managing ovarian cancer comprising administering to a patient in need thereof a therapeutically effective amount of Compound A, or a pharmaceutically acceptable salt, solvate, stereoisomer, or isotopologue thereof, in combination with a therapeutically effective amount of a checkpoint inhibitor. In one embodiment, the ovarian cancer is newly diagnosed, relapsed, refractory, or relapsed and refractory. In one embodiment, the patient has received no prior systemic therapy for ovarian cancer. In one embodiment, the patient has received prior therapy for ovarian cancer. In one embodiment, the patient has demonstrated progression or intolerance on the prior therapy.

In one embodiment, provided herein is a method of treating or managing ovarian cancer comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing ovarian cancer comprising administering to a patient in need thereof a therapeutically effective amount of Compound A, or a pharmaceutically acceptable salt, solvate, stereoisomer, or isotopologue thereof, in combination with a therapeutically effective amount of nivolumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and nivolumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and nivolumab is administered at an amount and frequency as described herein (e.g., weekly in a 7 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered (e.g., orally) once daily for 5 consecutive days followed by 2 days of rest in one or more 7 days cycles; and nivolumab is administered (e.g., intravenously) once every 2 weeks. In another embodiment, Compound A, or a pharmaceutically acceptable salt, solvate, stereoisomer, or isotopologue thereof, is administered (e.g., orally) at a dose of about 2 mg once daily for 5 consecutive days followed by 2 days of rest in one or more 7 days cycles; and nivolumab is administered (e.g., intravenously) at a dose of about 3 mg/kg once every 2 weeks. In one embodiment, the combination therapy is administered for 1 to 13 cycles of 7 days (e.g., about 3 months).

In one embodiment, provided herein is a method of treating or managing lung cancer (e.g., non-small cell lung cancer) comprising administering to a patient in need thereof a therapeutically effective amount of Compound A, or a pharmaceutically acceptable salt, solvate, stereoisomer, or isotopologue thereof, in combination with a therapeutically effective amount of a checkpoint inhibitor. In one embodiment, the lung cancer is newly diagnosed, relapsed, refractory, or relapsed and refractory. In one embodiment, the patient has received no prior systemic therapy for lung cancer. In one embodiment, the patient has received prior therapy for lung cancer. In one embodiment, the patient has demonstrated progression or intolerance on the prior therapy.

In one embodiment, provided herein is a method of treating or managing lung cancer (e.g., non-small cell lung cancer) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing lung cancer (e.g., non-small cell lung cancer) comprising administering to a patient in need thereof a therapeutically effective amount of Compound A, or a pharmaceutically acceptable salt, solvate, stereoisomer, or isotopologue thereof, in combination with a therapeutically effective amount of nivolumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and nivolumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and nivolumab is administered at an amount and frequency as described herein (e.g., weekly in a 7 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered (e.g., orally) once daily for 5 consecutive days followed by 2 days of rest in one or more 7 days cycles; and nivolumab is administered (e.g., intravenously) once every 2 weeks. In another embodiment, Compound A, or a pharmaceutically acceptable salt, solvate, stereoisomer, or isotopologue thereof, is administered (e.g., orally) at a dose of about 2 mg once daily for 5 consecutive days followed by 2 days of rest in one or more 7 days cycles; and nivolumab is administered (e.g., intravenously) at a dose of about 3 mg/kg once every 2 weeks. In one embodiment, the combination therapy is administered for 1 to 13 cycles of 7 days (e.g., about 3 months).

In one embodiment, provided herein is a method of treating or managing brain tumor (e.g., glioma) comprising administering to a patient in need thereof a therapeutically effective amount of Compound A, or a pharmaceutically acceptable salt, solvate, stereoisomer, or isotopologue thereof, in combination with a therapeutically effective amount of a checkpoint inhibitor. In one embodiment, the brain tumor is newly diagnosed, relapsed, refractory, or relapsed and refractory. In one embodiment, the patient has received no prior systemic therapy for brain tumor. In one embodiment, the patient has received prior therapy for brain tumor. In one embodiment, the patient has demonstrated progression or intolerance on the prior therapy.

In one embodiment, provided herein is a method of treating or managing brain tumor (e.g., glioma) comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/ discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing brain tumor (e.g., glioma) comprising administering to a patient in need thereof a therapeutically effective amount of Compound A, or a pharmaceutically acceptable salt, solvate, stereoisomer, or isotopologue thereof, in combination with a therapeutically effective amount of nivolumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and nivolumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and nivolumab is administered at an amount and frequency as described herein (e.g., weekly in a 7 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered (e.g., orally) once daily for 5 consecutive days followed by 2 days of rest in one or more 7 days cycles; and nivolumab is administered (e.g., intravenously) once every 2 weeks. In another embodiment, Compound A, or a pharmaceutically acceptable salt, solvate, stereoisomer, or isotopologue thereof, is administered (e.g., orally) at a dose of about 2 mg once daily for 5 consecutive days followed by 2 days of rest in one or more 7 days cycles; and nivolumab is administered (e.g., intravenously) at a dose of about 3 mg/kg once every 2 weeks. In one embodiment, the combination therapy is administered for 1 to 13 cycles of 7 days (e.g., about 3 months).

In one embodiment, provided herein is a method of treating or managing colorectal cancer comprising administering to a patient in need thereof a therapeutically effective amount of Compound A, or a pharmaceutically acceptable salt, solvate, stereoisomer, or isotopologue thereof, in combination with a therapeutically effective amount of a checkpoint inhibitor. In one embodiment, the colorectal cancer is newly diagnosed, relapsed, refractory, or relapsed and refractory. In one embodiment, the patient has received no prior systemic therapy for colorectal cancer. In one embodiment, the patient has received prior therapy for colorectal cancer. In one embodiment, the patient has demonstrated progression or intolerance on the prior therapy.

In one embodiment, provided herein is a method of treating or managing colorectal cancer comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s). In one embodiment, Compound A, or a pharmaceutically acceptable salt, solvate, stereoisomer, or isotopologue thereof, is administered once daily for 21 consecutive days followed by 7 days of rest (e.g., no administration of the compound/discontinuation of treatment) in a 28 days cycle; and the CPI is administered prior to, concomitantly with, or subsequent to administration of Compound A on one or more days (e.g., on day 1 of cycle 1). In one embodiment, the combination therapy is administered for 1 to 13 cycles of 28 days (e.g., about 12 months). In another embodiment, Compound A, or a pharmaceutically acceptable salt, solvate, stereoisomer, or isotopologue thereof, is administered once daily for 5 consecutive days followed by 2 days of rest (e.g., no administration of the compound/discontinuation of treatment) in a 7 days cycle; and the CPI is administered prior to, concomitantly with, or subsequent to administration of Compound A on one or more days (e.g., on day 1 of cycle 1). In one embodiment, the combination therapy is administered for 1 to 13 cycles of 7 days (e.g., about 3 months).

In one embodiment, provided herein is a method of treating or managing colorectal cancer comprising administering to a patient in need thereof a therapeutically effective amount of Compound A, or a pharmaceutically acceptable salt, solvate, stereoisomer, or isotopologue thereof, in combination with a therapeutically effective amount of nivolumab. In one embodiment, Compound A, or a pharmaceutically acceptable salt, solvate, stereoisomer, or isotopologue thereof, is administered at an amount and frequency as described herein (e.g., once daily for 21 consecutive days followed by 7 days of rest (e.g., no administration of the compound/discontinuation of treatment) in a 28 days cycle); and nivolumab is administered at an amount and frequency as described herein (e.g., monthly in a 28 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered at an amount and frequency as described herein (e.g., once daily for 5 consecutive days followed by 2 days of rest (e.g., no administration of the compound/discontinuation of treatment) in a 7 days cycle); and nivolumab is administered at an amount and frequency as described herein (e.g., weekly in a 7 day cycle) prior to, concomitantly with, or subsequent to administration of Compound A on one or more days (e.g., on day 1 of cycle 1). In another embodiment, Compound A, or a pharmaceutically acceptable salt, solvate, stereoisomer, or isotopologue thereof, is administered (e.g., orally) once daily for 5 consecutive days followed by 2 days of rest in one or more 7 days cycles; and nivolumab is administered (e.g., intravenously) once every 2 weeks. In another embodiment, Compound A, or a pharmaceutically acceptable salt, solvate, stereoisomer, or isotopologue thereof, is administered (e.g., orally) at a dose of about 2 mg once daily for 5 consecutive days followed by 2 days of rest in one or more 7 days cycles; and nivolumab is administered (e.g., intravenously) at a dose of about 3 mg/kg once every 2 weeks. In one embodiment, the combination therapy is administered for 1 to 13 cycles of 7 days (e.g., about 3 months).

In one embodiment of the methods provided herein, the patient has received one, two, three, or more prior therapies for the hematological cancer or solid tumor. In one embodiment, the patient has received one prior therapy for the hematological cancer or solid tumor. In one embodiment, the patient has received two prior therapies for the hematological cancer or solid tumor. In on embodiment, the patient has received three, or more prior therapies for the hematological cancer or solid tumor. In one embodiment, the patient has demonstrated progression or intolerance on one, two, three, or more prior therapies.

In one embodiment, the patient has received no prior therapies for the hematological cancer or solid tumor.

In one embodiment, the patient has minimal residual disease (MRD) after receiving a prior therapy. In one embodiment, the MRD level in the patient indicates that the patient has a high risk of becoming relapsed or refractory to the prior therapy. In one embodiment, the level of minimal residual disease in the patient is higher than a reference level. In one embodiment, the level of minimal residual disease in the patient is higher than 1 in 1000 cells.

In one embodiment, the patient has received allotransplantation.

In one embodiment, the patient is a pediatric or young adult patient.

In one embodiment, the methods provided herein further comprising administering a therapeutically or prophylactically effective amount of a second agent. The second agent is administered in combination with Compound A and the checkpoint inhibitor (e.g., triple therapy).

In one embodiment, provided herein is a method of treating, preventing, or managing a hematological cancer or solid tumor comprising administering to a patient in need thereof a therapeutically or prophylactically effective amount of Compound A of following formula, or a pharmaceutically acceptable salt, solvate, stereoisomer, or isotopologue thereof:

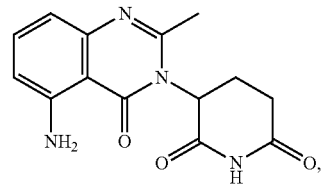 [SMILES: Cc1nc2cccc(N)c2c(=O)n1C1CCC(=O)NC1=O]

in combination with a therapeutically or prophylactically effective amount of one or more checkpoint inhibitor(s) and a second agent. In one embodiment, provided herein is a method of treating a hematological cancer or solid tumor comprising administering to a patient in need thereof a therapeutically effective amount of Compound A, or a pharmaceutically acceptable salt, solvate, stereoisomer, or isotopologue thereof, in combination with a therapeutically effective amount of one or more checkpoint inhibitor(s) and a second agent. In one embodiment, the second agent is 1) an anti-CD38 antibody, 2) an anti-CD19 antibody, 3) an anti-CD33 antibody, 4) an anti-CD20 antibody, 5) a FLT-3 inhibitor, or 6) a hypomethylating agent, or a combination thereof.

In one embodiment, the second agent is an anti-CD38 antibody. In one embodiment, the anti-CD38 antibody is isatuximab.

In one embodiment, the second agent is an anti-CD19 antibody. In one embodiment, the anti-CD19 antibody is blinatumomab.

In one embodiment, the second agent is an anti-CD33 antibody. In one embodiment, the anti-CD33 antibody is an antibody-drug conjugate. In one embodiment, the anti-CD33 antibody is SGN-CD33A (from SeattleGenetics). In one embodiment, the anti-CD33 antibody is a bispecific T-cell engager. In one embodiment, the anti-CD33 antibody is AMG 330 (from Amgen).

In one embodiment, the second agent is an anti-CD20 antibody. In one embodiment, the anti-CD19 antibody is rituximab.

In one embodiment, the second agent is a FLT-3 inhibitor. In one embodiment, the FLT-3 inhibitor is midostaurin, gilteritinib, or quizartinib. In one embodiment, the FLT-3 inhibitor is midostaurin. In one embodiment, the FLT-3 inhibitor is gilteritinib. In one embodiment, the FLT-3 inhibitor is quizartinib.

In one embodiment, the second agent is a hypomethylating agent. In one embodiment, the hypomethylating agent is guadecitabine (SGI-110), azacytidine, or decitibine. In one embodiment, the hypomethylating agent is guadecitabine. In one embodiment, the hypomethylating agent is azacytidine. In one embodiment, the hypomethylating agent is decitibine.

In one embodiment, a combination therapy as described herein is administered in combination with blinatumomab for treating acute lymphoblastic leukemia. In one embodiment, the AML is pediatric acute lymphoblastic leukemia. In one embodiment, the AML is adult acute lymphoblastic leukemia.

In one embodiment, a combination therapy as described herein is administered in combination with a FLT-3 inhibitor (e.g., midostaurin, gilteritinib, or quizartinib) for treating AML.

In one embodiment, a combination therapy as described herein is administered in combination with a hypomethylating agent (e.g., guadecitabine, azacytidine, or decitibine) for treating AML. In one embodiment, a combination therapy as described herein is administered in combination with a hypomethylating agent (e.g., guadecitabine, azacytidine, or decitibine) for treating MDS.

In one embodiment, a combination therapy as described herein is administered in combination with an anti-CD33 antibody (e.g., SGN-CD33A or AMG 330) for treating AML. In one embodiment, the patent has not received a prior therapy for AML. In one embodiment, the methods provided herein is used as first line therapy for the AML.

In certain embodiments, a combination therapy as described herein is administered with melphalan and dexamethasone to patients with amyloidosis. In certain embodiments, a combination therapy described herein and steroids can be administered to patients with amyloidosis.

In certain embodiments, a combination therapy as described herein is administered with gemcitabine and cisplatinum to patients with locally advanced or metastatic transitional cell bladder cancer.

In certain embodiments, a combination therapy as described herein is administered in combination with a secondary active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapsed brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a combination therapy as described herein is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a combination therapy as described herein is administered with temozolomide to patients with neuroendocrine tumors.

In certain embodiments, a combination therapy as described herein is administered with gemcitabine to patients with recurrent or metastatic head or neck cancer.

In certain embodiments, a combination therapy as described herein is administered with gemcitabine to patients with pancreatic cancer.

In certain embodiments, a combination therapy as described herein is administered to patients with colon cancer in combination with ARISA®, avastatin, taxol, and/or taxotere.

In certain embodiments, a combination therapy as described herein is administered with capecitabine and/or PLX4032 (Plexxikon) to patients with refractory colorectal cancer or patients who fail first line therapy or have poor performance in colon or rectal adenocarcinoma.

In certain embodiments, a combination therapy as described herein is administered in combination with fluorouracil, leucovorin, and irinotecan to patients with Dukes C & D colorectal cancer or to patients who have been previously treated for metastatic colorectal cancer.

In certain embodiments, a combination therapy as described herein is administered to patients with refractory colorectal cancer in combination with capecitabine, xeloda, and/or CPT-11.

In certain embodiments, a combination therapy as described herein is administered with capecitabine and irinotecan to patients with refractory colorectal cancer or to patients with unresectable or metastatic colorectal carcinoma.

In certain embodiments, a combination therapy as described herein is administered alone or in combination with interferon alpha or capecitabine to patients with unresectable or metastatic hepatocellular carcinoma; or with cisplatin and thiotepa to patients with primary or metastatic liver cancer.

In certain embodiments, a combination therapy as described herein is administered in combination with pegylated interferon alpha to patients with Kaposi's sarcoma.

In certain embodiments, a combination therapy as described herein is administered in combination with gemcitabine, abraxane, erlotinib, geftinib, and/or irinotecan to patients with non-small cell lung cancer.

In certain embodiments, a combination therapy as described herein is administered in combination with carboplatin and irinotecan to patients with non-small cell lung cancer.

In certain embodiments, a combination therapy as described herein is administered with doxetaxol to patients with non-small cell lung cancer who have been previously treated with carbo/VP 16 and radiotherapy.

In certain embodiments, a combination therapy as described herein is administered in combination with carboplatin and/or taxotere, or in combination with carboplatin, pacilitaxel and/or thoracic radiotherapy to patients with non-small cell lung cancer.

In certain embodiments, a combination therapy as described herein is administered in combination with taxotere to patients with stage IIIB or IV non-small cell lung cancer.

In certain embodiments, a combination therapy as described herein is administered in combination with oblimersen (Genasense®) to patients with small cell lung cancer.

In certain embodiments, a combination therapy as described herein is administered in combination with ABT-737 (Abbott Laboratories) and/or obatoclax (GX15-070) to patients with lymphoma and other blood cancers.

In certain embodiments, a combination therapy as described herein is administered alone or in combination with a secondary active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a combination therapy as described herein is administered in combination with taxotere, IL-2, IFN, GM-CSF, PLX4032 (Plexxikon) and/or dacarbazine to patients with various types or stages of melanoma.

In certain embodiments, a combination therapy as described herein is administered alone or in combination with vinorelbine to patients with malignant mesothelioma, or stage IIIB non-small cell lung cancer with pleural implants or malignant pleural effusion mesothelioma syndrome.

In certain embodiments, a combination therapy as described herein is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a combination therapy as described herein is administered to patients with relapsed or refractory multiple myeloma in combination with doxorubicin (Doxil®), vincristine and/or dexamethasone (Decadron®).

In certain embodiments, a combination therapy as described herein is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a combination therapy as described herein is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a combination therapy as described herein is administered to patients with various types or stages of renal cell cancer, in combination with capecitabine, IFN, tamoxifen, IL-2, GM-CSF, Celebrex®, or a combination thereof.

In certain embodiments, a combination therapy as described herein is administered to patients with various types or stages of gynecologic, uterus or soft tissue sarcoma cancer in combination with IFN, a COX-2 inhibitor such as Celebrex®, and/or sulindac.

In certain embodiments, a combination therapy as described herein is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a combination therapy as described herein is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) combination therapy as described herein. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a combination therapy as described herein, in certain embodiments, alleviates or reduces adverse effects which are of such severity that it would otherwise limit the amount of anti-cancer drug.

In one embodiment, Compound A, or a pharmaceutically acceptable salt, solvate, stereoisomer, or isotopologue thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, Compound A, or a pharmaceutically acceptable salt, solvate, stereoisomer, or isotopologue thereof, is administered in combination with specific agents such as heparin, aspirin, coumadin, or G-CSF to avoid adverse effects that are associated with anti-cancer drugs such as but not limited to neutropenia or thrombocytopenia.

In one embodiment, Compound A, or a pharmaceutically acceptable salt, solvate, stereoisomer, or isotopologue thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

The methods of treating, preventing, and/or managing described hereinabove can include combination therapies described herein that are administered using cycling therapy as described herein.

4.5 Administration of Combination Therapies

Combination therapies as described herein are administered without restriction on the order in which therapies are administered to a patient with a disease or disorder described herein. Thus, in one embodiment, a first therapy (e.g., Compound A) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a checkpoint inhibitor as described herein) to the subject. Such administration can be performed using cyclic administration as described herein. Triple therapy is also contemplated herein (e.g., addition of a second compound or checkpoint inhibitor as described herein, addition of a second therapeutic agent described herein or addition of another combination therapy as described herein).

Administration of the components of a combination therapy as described herein can occur simultaneously or sequentially as described above by the same or different routes of administration. The suitability of a particular route of administration employed for a particular active agent will depend on the active agent itself (e.g., whether it can be administered orally without decomposing prior to entering the blood stream) and the cancer being treated.

In certain embodiment, Compound A, or a pharmaceutically acceptable salt, solvate, stereoisomer, or isotopologue thereof, is administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound A, or a pharmaceutically acceptable salt, solvate, stereoisomer, or isotopologue thereof, is orally administered.

Compound A, or a pharmaceutically acceptable salt, solvate, stereoisomer, or isotopologue thereof, is administered at an amount of about 0.01 mg to about 100 mg per day, about 0.1 mg to about 75 mg per day, about 0.5 mg to about 50 mg per day, about 0.1 mg to about 25 mg per day, about 1 mg to about 25 mg per day, about 0.5 mg to about 10 mg per day, about 1 mg to about 10 mg per day, about 0.5 mg to about 5 mg per day, about 1 mg to about 5 mg per day, about 1 mg to about 3 mg per day, or about 2 mg to about 5 mg per day.

In one embodiment, Compound A, or a pharmaceutically acceptable salt, solvate, stereoisomer, or isotopologue thereof, is administered at an amount of about 1 mg to about 5 mg per day. In one embodiment, Compound A, or a pharmaceutically acceptable salt, solvate, stereoisomer, or isotopologue thereof, is administered at an amount of about 1 mg per day. In one embodiment, Compound A, or a pharmaceutically acceptable salt, solvate, stereoisomer, or isotopologue thereof, is administered at an amount of about 2 mg per day. In one embodiment, Compound A, or a pharmaceutically acceptable salt, solvate, stereoisomer, or isotopologue thereof, is administered at an amount of about 3 mg per day. In one embodiment, Compound A, or a pharmaceutically acceptable salt or solvate thereof, is administered at an amount of about 4 mg per day. In one embodiment, Compound A, or a pharmaceutically acceptable salt or solvate thereof, is administered at an amount of about 5 mg per day.

In one embodiment, Compound A, or a pharmaceutically acceptable salt, solvate, stereoisomer, or isotopologue thereof, is administered once daily for 28 consecutive days in a 28 days cycle. In one embodiment, Compound A, or a pharmaceutically acceptable salt, solvate, stereoisomer, or isotopologue thereof, is administered once daily for 5 consecutive days followed by 2 days of no administration in a 28 days cycle. In one embodiment, Compound A, or a pharmaceutically acceptable salt, solvate, stereoisomer, or isotopologue thereof, is administered once daily for 21 consecutive days followed by 7 days of no administration in a 28 days cycle.

Compound A, or a pharmaceutically acceptable salt, solvate, stereoisomer, or isotopologue thereof, and the checkpoint inhibitor, or a pharmaceutically acceptable salt or solvate thereof, may be administered using the same route or via different routes. Compound A, or a pharmaceutically acceptable salt, solvate, stereoisomer, or isotopologue thereof, and the checkpoint inhibitor, or a pharmaceutically acceptable salt or solvate thereof, may be administered simultaneously or sequentially. Compound A, or a pharmaceutically acceptable salt, solvate, stereoisomer, or isotopologue thereof, and the checkpoint inhibitor, or a pharmaceutically acceptable salt or solvate thereof, may be administered in one pharmaceutical composition or in separate compositions.

In certain embodiments, the checkpoint inhibitors provided herein can be administered according to the routes and dosage amounts generally known to a person of ordinary skill in the art.

Checkpoint inhibitors described herein for use in a combination therapy described herein can be administered in amounts from about 0.005 to about 2,000 mg per day, from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day. In one embodiment a checkpoint inhibitor described herein is administered in an amount from about 500 mg to about 2500 mg, 750 mg to about 2250 mg, 1000 mg to about 2000 mg, or about 1200 mg to about 1800 mg.

Checkpoint inhibitors described herein can be administered in a therapeutically effective amount of about 100, 200, 300, 400, 500, 600, 700, 800, 900, 1000, 1100, 1200, 1300, 1400, 1500, 1600, 1700, 1800, 1900, 2000, 2100, 2200, 2300, 2400, or about 2500 mg. In certain embodiments the checkpoint inhibitor is administered in a therapeutically effective amount of about 1000, 1250, 1500, 1750, or 2000 mg.

In one embodiment the checkpoint inhibitor is a PD-L1 inhibitor. In one embodiment the PD-L1 inhibitor is durvalumab. Durvalumab can be administered in an amount from 1 mg to about 2,000 mg per day, from about 100 mg to about 2,000 mg per day, from about 250 mg to about 2,000 mg per day, from about 500 mg to about 2,000 mg per day, 1 mg to about 1,500 mg per day, from about 100 mg to about 1,500 mg per day, from about 250 mg to about 1,500 mg per day, from about 500 mg to about 1,500 mg per day, 1 mg to about 1,000 mg per day, from about 100 mg to about 1,000 mg per day, from about 250 mg to about 1,000 mg per day, from about 500 mg to about 1,000 mg per day, from about 250 mg to about 750 mg per day, or from about 400 mg to about 600 mg per day. In another embodiment the checkpoint inhibitor is durvalumab administered at an amount of about 100, 250, 500, 1,000, 1,500, or 2,000 mg per day. In one embodiment, durvalumab is administered at a concentration of about 50 mg/mL. In one embodiment, a combination therapy as described herein is co-administered to a patient receiving radiation therapy (e.g., local involved field radiation therapy (IFRT)).

In one embodiment of the methods provided herein, the checkpoint inhibitor is nivolumab, and it is administered intravenously. In one embodiment, nivolumab is administered at a dose of from about 0.1 mg/kg to about 5 mg/kg, from about 0.1 mg/kg to about 3 mg/kg, from about 0.1 mg/kg to about 2 mg/kg, from about 0.1 mg/kg to about 1 mg/kg, or from about 0.1 mg/kg to about 0.5 mg/kg every 2 weeks. In one embodiment, nivolumab is administered at a dose of about 3 mg/kg, about 2.5 mg/kg, about 2 mg/kg, about 1.5 mg/kg, about 1 mg/kg, or about 0.5 mg/kg every 2 weeks. In one embodiment, nivolumab is administered at a dose of about 3 mg/kg every 2 weeks.

In certain embodiments, compounds provided herein can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug).

The route of administration of Compound A, or a pharmaceutically acceptable salt, solvate, stereoisomer, or isotopologue thereof, is independent of the route of administration of a checkpoint inhibitor as described herein. In one embodiment, Compound A, or a pharmaceutically acceptable salt, solvate, stereoisomer, or isotopologue thereof, is administered orally (PO). In another embodiment, Compound A, or a pharmaceutically acceptable salt, solvate, stereoisomer, or isotopologue thereof, is administered intravenously (IV). In one embodiment, Compound A, or a pharmaceutically acceptable salt, solvate, stereoisomer, or isotopologue thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, Compound A, or a pharmaceutically acceptable salt, solvate, stereoisomer, or isotopologue thereof, and a checkpoint inhibitor provided herein are administered by the same mode of administration, e.g., orally or by IV. In another embodiment, Compound A, or a pharmaceutically acceptable salt, solvate, stereoisomer, or isotopologue thereof, is administered by one mode of administration, e.g., by PO, whereas a checkpoint inhibitor provided herein is administered by another mode of administration, e.g., IV.

4.6 Combination with Secondary Active Agents

In certain embodiments, Compound A, or a pharmaceutically acceptable salt, solvate, stereoisomer, or isotopologue thereof, and the checkpoint inhibitor, or a pharmaceutically acceptable salt or solvate thereof, may be administered in combination with one or more secondary active agents. Such therapies are referred to herein as "triple therapies."

When used in this context, the term "in combination" includes the use of a combination therapy as described herein with one or more secondary active agents (e.g., prophylactic and/or therapeutic agents) described herein. Administration of a secondary active agent in combination with a combination therapy as described herein does not restrict the order in which any of therapies are administered to a patient with a disease or disorder. Accordingly, a first therapy and a second therapy can be administered as set forth above and one or more secondary active agents can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of either of the agents in the combination therapy.

Administration of secondary active agents is independent of the route of administration for the combination therapies described herein, including each component (e.g., Compound A or checkpoint inhibitor described herein). The suitability of a particular route of administration employed for a particular secondary active agent will depend on the active agent itself (e.g., whether it can be administered orally without decomposing prior to entering the blood stream), the cancer being treated, and patient tolerance.

The secondary active agent can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In certain embodiments a secondary active agent is administered orally or by IV. In some embodiments, the secondary active agent is formulated together with a combination therapy as described herein. Such formulations include those set forth herein and can be supplied as components of kits described herein.

Examples of such secondary agents include, but are not limited to: Abraxane®; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other examples include, but are not limited to: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer. In one embodiment, the secondary active agent is ibrutinib, bendamustine, or rituximab (a CD20 specific chimeric murine/human monoclonal antibody).

In certain embodiments, the secondary active agent is oblimersen)(GENASENSE®, GM-CSF, G-CSF, SCF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In one embodiment, the secondary active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the secondary active agent will depend on the specific agent used, the type of disease being treated or managed, the severity and stage of disease, and the amount of any optional additional active agents concurrently administered to the patient.

The secondary active agent can be administered using cyclic therapy as described herein.

In one embodiment the secondary active agent is rituximab can be administered at a concentration of 375 mg/m$^2$. In one embodiment, rituximab is administered on days 1 and 8 of cycle 1 (e.g., the first cycle) at a concentration of 375 mg/m$^2$. In another embodiment, rituximab is administered at 375 mg/m$^2$ once weekly (e.g., days 2, 8, 15, and 22 of cycle 1) and on day one of each subsequent cycle (e.g., 2-5 cycles). Rituximab can further be administered on day one of every additional cycle in a 28-day cycle at a concentration of 500 mg/m$^2$. In such embodiments, rituximab can be administered over 1, 2, 3, 4, 5, 6, 7, 8, 9, 10, or 11 cycles and optionally between 1-5 total cycles. Secondary active agents described herein can be administered in accordance with established protocols (e.g., marketed compositions).

In certain embodiments, when the secondary active agent is GM-CSF, G-CSF, SCF or EPO, such secondary active agents are administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, when the secondary active agent is GM-CSF, it may be administered in an amount of from about 60 to about 500 mcg/m$^2$ intravenously over 2 hours or from about 5 to about 12 mcg/m$^2$/day subcutaneously. In certain embodiments, when the secondary active agent is G-CSF, it may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, when the secondary active agent is EPO, it may be administered subcutaneously in an amount of 10,000 Unit 3 times per week.

4.7 Cycling Therapy

In some embodiment, the components of the combination therapies described herein (e.g., Compound A and a CPI as described herein) are cyclically administered to a patient. In another embodiment, a secondary active agent is co-administered in a cyclic administration with the combination therapies provided herein. Cycling therapy involves the administration of an active agent for a period of time, followed by a rest for a period of time, and repeating this sequential administration. Cycling therapy can be performed independently for each active agent (e.g., Compound A, a CPI described herein, and/or a secondary agent described herein) over a prescribed duration of time. In certain embodiments, the cyclic administration of each active agent is dependent upon one or more of the active agents administered to the subject. In one embodiment, administration of Compound A or a checkpoint inhibitor described herein fixes the day(s) or duration of administration of each agent. In another embodiment, administration of Compound A or a checkpoint inhibitor described herein fixes the days(s) or duration of administration of a secondary active agent.

In some embodiments, Compound A, or a pharmaceutically acceptable salt, solvate, stereoisomer, or isotopologue thereof, a CPI described herein, and/or a secondary active agent described herein is administered continually (e.g., daily, weekly, monthly) without a rest period. Cycling therapy can reduce the development of resistance to one or more of the therapies, avoid, or reduce the side effects of one of the therapies, and/or improve the efficacy of the treatment or therapeutic agent.

In one embodiment, Compound A, or a pharmaceutically acceptable salt, solvate, stereoisomer, or isotopologue thereof, is administered as a component of a combination therapy as described herein once daily for 28 consecutive days in a 28 days cycle. Such combination therapies comprises administration of a CPI as described herein prior to, concomitantly with, or subsequent to administration of Compound A on one or more days (e.g., on day 1 of cycle 1). In another embodiment, a compound as described herein is administered once daily for 21 consecutive days followed by 7 days of rest (e.g., no administration of the compound/discontinuation of treatment) in a 28 days cycle. Such a combination therapy comprises administration of a CPI as described herein prior to, concomitantly with, or subsequent to administration of Compound A on one or more days (e.g., on day 1 of cycle 1). In one embodiment, the combination therapy is administered for 1 to 13 cycles of 28 days (e.g., about 12 months). Compound A, or a pharmaceutically acceptable salt, solvate, stereoisomer, or isotopologue thereof, and CPIs described herein of such a combination can be present at a concentration or amount as set forth herein. In one embodiment the combination therapy comprises administration of Compound A, or a pharmaceutically acceptable salt, solvate, stereoisomer, or isotopologue thereof, consecutively for 21 days of a 28 days cycle and administration of a CPI on at least one day of each cycle (e.g., day 1 of cycle 1) in combination with a secondary active agent administered on at least one day of each cycle. In certain embodiments, the secondary active agent can be administered once daily, once weekly, or once monthly during the cycling therapy. In another embodiment, the secondary active agent is administered once weekly in combination with a combination therapy described herein.

In one embodiment, Compound A, or a pharmaceutically acceptable salt, solvate, stereoisomer, or isotopologue thereof, is administered as a component of a combination therapy as described herein once daily for 7 consecutive days in a 7 days cycle. Such combination therapies comprises administration of a CPI as described herein prior to, concomitantly with, or subsequent to administration of Compound A on one or more days (e.g., on day 1 of cycle 1). In another embodiment, a compound as described herein is administered once daily for 5 consecutive days followed by 2 days of rest (e.g., no administration of the compound/discontinuation of treatment) in a 7 days cycle. Such a combination therapy comprises administration of a CPI as described herein prior to, concomitantly with, or subsequent to administration of Compound A on one or more days (e.g., on day 1 of cycle 1). In one embodiment, the combination therapy is administered for 1 to 13 cycles of 28 days (e.g., about 3 months). Compound A, or a pharmaceutically acceptable salt, solvate, stereoisomer, or isotopologue thereof, and CPIs described herein of such a combination can be present at a concentration or amount as set forth herein. In one embodiment the combination therapy comprises administration of Compound A, or a pharmaceutically acceptable salt, solvate, stereoisomer, or isotopologue thereof, consecutively for 5 days of a 7 days cycle and administration of a CPI on at least one day of each cycle (e.g., day 1 of cycle 1) in combination with a secondary active agent administered on at least one day of each cycle. In certain embodiments, the secondary active agent can be administered once daily, once weekly, or once monthly during the cycling therapy. In another embodiment, the secondary active agent is administered once weekly in combination with a combination therapy described herein.

A compound for use in combination therapies described herein can independently be administered once daily (QD), or divided into multiple daily doses such as twice daily (BID), three times daily (TID), and four times daily (QID) as part of a combination therapy described herein. In addition, the administration can be continuous (i.e., daily for consecutive days or every day), intermittent, e.g., in cycles (i.e., including days, weeks, or months of rest without drug). As used herein, the term "daily" is intended to mean that a therapeutic agent is administered once or more than once each day, for example, for a period of time. The term "continuous" is intended to mean that a therapeutic agent is administered daily for an uninterrupted period of at least 10 days to 52 weeks. The term "intermittent" or "intermittently" as used herein is intended to mean stopping and starting at either regular or irregular intervals. For example, intermittent administration of a compound for use in combination therapies described herein can be administered for one to six days per week, administration in cycles (e.g., daily administration for two to eight consecutive weeks, then a rest period with no administration for up to one week), or administration on alternate days. The term "cycling" as used herein is intended to mean that a therapeutic agent is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a compound for use in combination therapies described herein is administered once a day. In another embodiment, a compound for use in combination therapies described herein is administered twice a day. In yet another embodiment, a compound for use in combination therapies described herein is administered three times a day. In still another embodiment, a compound for use in combination therapies described herein is administered four times a day.

In certain embodiments, a compound for use in combination therapies described herein is administered once per day from one day to six months, from one week to three months, from one week to four weeks, from one week to three weeks, or from one week to two weeks. In certain embodiments, a compound for use in combination therapies described herein is administered once per day for one week, two weeks, three weeks, or four weeks. In one embodiment, a compound for use in combination therapies described herein is administered once per day for one week. In another embodiment, a compound for use in combination therapies described herein is administered once per day for two weeks. In yet another embodiment, a compound for use in combination therapies described herein is administered once per day for three weeks. In still another embodiment, a compound for use in combination therapies described herein is administered once per day for four weeks.

A checkpoint inhibitor for use in combination therapies described herein can independently be administered once daily (QD), or divided into multiple daily doses such as twice daily (BID), three times daily (TID), and four times daily (QID) as part of a combination therapy described herein. In addition, the administration can be continuous (i.e., daily for consecutive days or every day), intermittent, e.g., in cycles (i.e., including days, weeks, or months of rest without drug). As used herein, the term "daily" is intended to mean that a therapeutic agent is administered once or more than once each day, for example, for a period of time. The term "monthly" is intended to mean that a therapeutic agent is administered once a month or about every 4 weeks for an uninterrupted period of time equal to the number of cycles of administration. The term "continuous" is intended to mean that a therapeutic agent is administered daily for an uninterrupted period of at least 10 days to 52 weeks. The term "intermittent" or "intermittently" as used herein is intended to mean stopping and starting at either regular or irregular intervals. For example, intermittent administration of a checkpoint inhibitor for use in combination therapies described herein can be administered for one to six days per week, administration in cycles (e.g., daily administration for two to eight consecutive weeks, then a rest period with no administration for up to one week), or administration on alternate days. For example, intermittent administration of a checkpoint inhibitor for use in combination therapies described herein can be administered for once per month, administration in cycles (e.g., monthly administration for two to twelve cycles).

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, a checkpoint inhibitor for use in combination therapies described herein is administered once a month. In another embodiment, a checkpoint inhibitor for use in combination therapies described herein is administered twice a month. In yet another embodiment, a checkpoint inhibitor for use in combination therapies described herein is administered three times a month. In still another embodiment, a checkpoint inhibitor for use in combination therapies described herein is administered four times a month (e.g., weekly).

4.8 Pharmaceutical Compositions

In one embodiment, provided herein are pharmaceutical compositions and dosage forms, which comprise: (1) Compound A, or an enantiomer or a mixture of enantiomers thereof, or a pharmaceutically acceptable salt, solvate, hydrate, co-crystal, clathrate, or polymorph thereof; (2) and the checkpoint inhibitor, or a pharmaceutically acceptable salt or solvate thereof; or (3) a mixture thereof. In another embodiment, pharmaceutical compositions and dosage forms further comprise one or more excipients.

In certain embodiments, pharmaceutical compositions and dosage forms provided herein also comprise one or more additional active ingredients. Examples of optional second, or additional, active ingredients are disclosed herein elsewhere.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal, or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein may vary depending on their use. For example, a dosage form used in the acute treatment of a disease may contain larger amounts of one or more of the active ingredients than a dosage form used in the chronic treatment of the same disease. Similarly, a parenteral dosage form may contain smaller amounts of one or more of the active ingredients than an oral dosage form used to treat the same disease. See, e.g., Remington's Pharmaceutical Sciences, 18th ed., Mack Publishing, Easton Pa. (1990).

Whether a particular excipient is suitable for incorporation into a pharmaceutical composition or dosage form provided herein depends on a variety of factors, including, but not limited to, the route of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, encompassed herein are pharmaceutical compositions and dosage forms that contain little, if any, lactose. As used herein, the term "lactose-free" means that the amount of lactose present, if any, is insufficient to substantially increase the degradation rate of an active ingredient.

Lactose-free compositions provided herein can comprise excipients that are listed, for example, in the U.S. Pharmacopeia (USP) 25 NF20 (2002). In certain embodiments, lactose-free compositions comprise active ingredients, a binder/filler, and a lubricant in pharmaceutically compatible and pharmaceutically acceptable amounts. In certain embodiments, lactose-free dosage forms comprise active ingredients, microcrystalline cellulose, pre-gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, in certain embodiments, provided herein are anhydrous compositions packaged using materials to prevent exposure to water such that they can be included in suitable formulary kits. Examples of suitable packaging include, but are not limited to, hermetically sealed foils, plastics, unit dose containers (e.g., vials), blister packs, and strip packs.

Encompassed herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

In certain embodiments, the dosage forms provided herein comprise Compound A, or an enantiomer or a mixture of enantiomers thereof, or a pharmaceutically acceptable salt, solvate, hydrate, co-crystal, clathrate, or polymorph thereof, in an amount ranging from about 0.10 to about 1000 mg, from about 0.10 to about 500 mg, from about 0.10 to about 200 mg, from about 0.10 to about 150 mg, from about 0.10 to about 100 mg, from about 0.10 to about 50 mg, from about 0.5 to about 10 mg, or from about 1 to about 5 mg. In certain embodiments, the dosage forms provided herein comprise Compound A, or an enantiomer or a mixture of enantiomers thereof, or a pharmaceutically acceptable salt, solvate, hydrate, co-crystal, clathrate, or polymorph thereof, in an amount of about 0.1, about 1, about 2, about 3, about 4, about 5, about 7.5, about 10, about 12.5, about 15, about 17.5, about 20, about 25, about 50, about 100, about 150, or about 200 mg.

In certain embodiments, the dosage forms provided herein comprise the checkpoint inhibitor, or a pharmaceutically acceptable salt or solvate thereof, in an amount ranging from about 1 to about 1000 mg, from about 10 to about 800 mg, from about 50 to about 600 mg, from about 100 to about 700 mg, from about 100 to about 500 mg, from about 300 to about 500 mg, from about 200 to about 400 mg, or from about 350 to about 450 mg. In certain embodiments, the dosage forms provided herein comprise Compound A, or an enantiomer or a mixture of enantiomers thereof, or a pharmaceutically acceptable salt, solvate, hydrate, co-crystal, clathrate, or polymorph thereof, in an amount of about 50, about 100, about 200, about 300, about 400, about 500, about 600, about 700, about 800, about 900, or about 1000 mg.

4.8.1 Oral Dosage Forms

In certain embodiments, pharmaceutical compositions provided herein that are suitable for oral administration are formulated as discrete dosage forms, examples of which include, but are not limited to, tablets (e.g., chewable tablets), caplets, capsules, and liquids (e.g., flavored syrups). Such dosage forms contain predetermined amounts of active ingredients and may be prepared by some known methods of pharmacy. See generally, Remington's Pharmaceutical Sciences, 18th ed., Mack Publishing, Easton Pa. (1990).

In certain embodiments, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms may be prepared by some known methods of pharmacy. In certain embodiments, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet is prepared by compression or molding. In certain embodiments, compressed tablets are be prepared by compressing in a suitable machine the active ingredients in a free-flowing form, e.g., powder or granules, optionally mixed with an excipient. In certain embodiments, molded tablets are made by molding in a suitable machine a mixture of a powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms provided herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, AVICEL-PH-101, AVICEL-PH-103 AVI-CEL RC-581, AVICEL-PH-105 (FMC Corporation, American Viscose Division, Avicel Sales, Marcus Hook, Pa.), and mixtures thereof. An specific binder is a mixture of microcrystalline cellulose and sodium carboxymethyl cellulose (e.g., AVICEL RC-581). Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein is present in from about 50 to about 99 weight percent of the pharmaceutical composition or dosage form.

Disintegrants are used in the compositions provided herein to provide tablets the ability to disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation. In certain embodiments, the pharmaceutical compositions provided herein comprise from about 0.5 to about 15 weight percent or from about 1 to about 5 weight percent of disintegrant.

Disintegrants that are suitable for use in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that are suitable for use in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, but are not limited to, a syloid silica gel (AEROSIL200, W.R. Grace Co., Baltimore, Md.), a coagulated aerosol of synthetic silica (Degussa Co. of Plano, Tex.), CAB-O-SIL (a pyrogenic silicon dioxide, Cabot Co. of Boston, Mass.), and mixtures thereof. In certain embodiments, if used at all, lubricants are used in an amount of less than about 1 weight percent of the pharmaceutical compositions or dosage forms into which they are incorporated.

4.8.2 Delayed Release Dosage Form

In certain embodiments, the active ingredients provided herein are administered by controlled release means or by delivery devices. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated herein by reference in its entirety. In certain embodiments, such dosage forms are be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Encompassed herein are single unit dosage forms suitable for oral administration, including, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.8.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Some suitable vehicles that can be used to provide parenteral dosage forms provided herein include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of a compound provided herein. See, e.g., U.S. Pat. No. 5,134,127, the disclosure of which is incorporated herein by reference in its entirety.

4.8.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein depend on the particular tissue to which a given pharmaceutical composition or dosage form will be applied. With that fact in mind, in certain embodiments, the excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Additional examples of such ingredients can be found, e.g., in Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.8.5 Kits

In certain embodiments, compounds provided herein are not administered to a patient at the same time or by the same route of administration. Therefore, encompassed herein are kits which, when used by the medical practitioner, can simplify the administration of appropriate amounts of active ingredients to a patient.

In certain embodiments, a kit provided herein comprises a dosage form of a compound provided herein. In certain embodiments, the kit provided herein further comprises additional active ingredients. Examples of the additional active ingredients include, but are not limited to, those disclosed herein elsewhere.

In certain embodiments, the kit provided herein further comprises a device that is used to administer the active ingredients. Examples of such devices include, but are not limited to, syringes, drip bags, patches, and inhalers.

In certain embodiments, the kit provided herein further comprises cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

The examples below are carried out using standard techniques, which are well known and routine to those of skill in the art, except where otherwise described in detail. The examples are intended to be merely illustrative.

5.1 Orthotopic HCC Model

The effects of Compound A in combination with checkpoint inhibitors were investigated in an orthotopic HCC model. The orthotopic HCC model was established by injecting about $2 \times 10^5$ murine liver cancer cell line (BNL-1MEA) cells into the sub-capsular area of the left liver lobe of male BALB/c or SCID mice at age of 6-7 weeks.

5.1.1 In Vitro Drug Treatment and Efficacy/Safety Evaluation

Cell viability is measured by MTT (3-(4,5-Dimethylthiazol-2-yl)-2,5 diphenyltetrazolium bromide) assay and the extent of apoptosis is measured by flow cytometry (sub-G1 fraction analysis) after 72 hours of drug treatment.

5.1.2 In Vivo Drug Treatment and Efficacy/Safety Evaluation

Mice were randomized to different treatment groups on day 6 after tumor implantation. Tumor volumes were measured after 22 days of treatment with Compound A alone, the checkpoint inhibitor alone, and Compound A in combination with the checkpoint inhibitor by using the following formula: volume $[mm^3]=[width]^2 \times length \times 0.5$.

Blood samples were obtained via cardiac puncture after 22 days of drug treatment to check the hematology and blood biochemistry data. Hematology data were measured by an automated hematology analyzer (Medonic CA620 VET, Boule Medical AB, Sweden). Blood biochemistry data were measured by an automated dry-chemistry analyzer system (Spotchem SP-4410; Kyoto Daiichi-kagaku, Kyoto, Japan).

5.1.3 Tumor Apoptosis and Angiogenesis

Formalin-fixed, paraffin-embedded tumor samples are collected at the end of drug treatment. Slides of 5-μm thick sections are prepared for analysis of tumor apoptosis (TUNEL assay, DeadEnd Fluorometric TUNEL System) and tumor angiogenesis (CD31 immunohistochemical staining).

The vascular normalization index (VNI) is calculated using the following formula:

$$VNI = MVD \times (Density_{\alpha\text{-}SMA}/Density_{Collagen\ IV}).$$

MVD (microvessel density) is determined by IHC staining with CD31 antibody. $Density_{\alpha\text{-}SMA}$ and $Density_{Collagen\ IV}$ is determined by IHC staining with respective antibodies.

5.1.4 Isolation/Quantification of Tumor-Infiltrating Lymphocytes and Intra-CellularStaining Tumor tissues were cut into small pieces, followed by incubation with HBSS containing collagenase type I (0.05 mg/ml), collagenase type IV (0.05 mg/ml), hyaluronidase (0.025 mg/ml), DNase (0.01 mg/ml) and soybean trypsin inhibitor (1 mg/ml) (all from Sigma-Aldrich) for 15 minutes. TILs were recovered by using Ficoll-Paque gradient and subjected to lymphocyte subpopulations analysis by flow cytometry (FACScan Caliber, Becton Dickinson; data processed by using the CELLQest Pro Software, BD Biosciences Pharmingen). CD4+ T cells, CD8+ T cells, NK cells, or NKT cells were determined by double staining with specific antibodies recognizing murine CD3 (clone 145-2C11), CD4 (cone GK1.5), CD8 (clone 53-6.7), or Pan-NK (clone DX5)(BD Biosciences Pharmingen).

Staining of intracellular molecules, including interferon-γ (IFN-γ), FoxP3, granzyme B, and perforin, were performed to determine the activation status of cytotoxic CD8+ lymphocytes. Cells were fixed after surface marker staining and permeabilized according to the manufacturer protocol (BD Biosciences Pharmingen), and then stained with allophycocyanin-conjugated anti-IFN-γ (clone XMG1.2), anti-FoxP3 (clone MF23) (BD Biosciences Pharmingen), anti-granzyme B (clone NGZB), or anti-perforin (eBioOMAK-D) antibodies, respectively.

5.1.5 In Vitro Natural Killer Cytolytic Activities of Splenocytes

Lactate dehydrogenase (LDH) assay (Promega) is used. $2 \times 10^4$ YAC-1 cells are incubated with effector cells at effector cells/target cells ratios of 0.1, 1 and 10 for 195 minutes at 37° C., 5% $CO_2$. LDH released by lysed target cells is quantified by colorimetry (OD value at 490 nm). Target cells are incubated either in culture medium alone or in a mixture of 2% Triton X-100 to determine spontaneous and maximal LDH release, respectively. The percentage of specific lysis are calculated by the following formula: percent cytotoxicity=[(experimental LDH release–spontaneous LDH release by effector and target)/(maximal LDH release–spontaneous LDH release)]×100.

5.1.6 Depletion of Pertinent Cellular Immune Effectors and Cytokines

To evaluate the roles of cellular immune effectors and cytokines in the anti-tumor efficacy of Compound A and checkpoint inhibitors, $CD8^+$ T cells cells are depleted by intraperitoneal injection of anti-CD8 (clone 53-6.72), or isotype controls (clone 2A3 or HRPN) (all from BioXCell, West Lebanon, N.H.), respectively. The dosage of antibody treatment is 0.5 mg on day 5, and then 0.25 mg on days 8, 11, 14, and 17 after tumor implantation. Depletion of $CD8^+$ cells is confirmed by flow cytometry.

5.1.7 Cytokine Assay

Six cytokines (IL-2, IL-4, IL-10, IL-17, IFN-γ and TNF-α) from TILs and serum samples obtained from mice after 22 days of study drug treatment are quantified by using Procarta® Cytokine Assay Plex Kits (Affymetrix, Inc. Santa Clara, Calif., USA), in accordance with the manufacturer's instructions. All collected samples are immediately stored at −70° C. and remained in storage until testing. After the plate is analyzed using the Luminex instrument, LABScan 100 (Luminex Corporation. Austin, USA).

5.1.8 Pharmacokinetic Studies of Compound A

Blood samples from animals treated with Compound A are collected at specific time points (e.g., baseline, 0.5, 2, 4, 8, and 24 hr after treatment; 2 mice per time point) by direct cardiac puncture. The samples are centrifuged at a temperature of 2-8° C., at 3,000 rpm, for 5 minutes and then immediately placed on ice. A 150 μL aliquot of plasma is transferred to a labeled tube containing an equal volume of Sorensen's buffer and mixed well.

5.1.9 Overexpression of PDL1 and PDL2 In Vitro

For stable transfection, BNL-MEA1 cells were transfected with the pCMV6-mPDL1-Myc-DDK vector (MR203953; Origene Technologies, Rockville, Md.), pCMV6-mPDL2-Myc-DDK vector (MR222499; Origene Technologies) or empty vector (pCMV6 vector; Origene Technologies, Rockville, Md.) using Lipofectamine 2000 transfection reagent (Invitrogen, Carlsbad, Calif., USA), optimized according to the manufacturer's instructions.

The transfected cells were selected with G418 (500 μg/ml; Sigma, St Louis, Mo., USA) for 3 weeks (the medium was changed every 3 days). G418-resistant colonies were selected and grown/amplified to obtain stable cell lines. Expression of PDL1 or PDL2 were confirmed by Western blot and immunofluorescence assay.

5.1.10 Effects of Combination

The anti-tumor effects of combination of Compound A with anti-CTLA-4 antibody (Bristol-Myers Squibb) was tested in the orthotopic liver cancer model and the results are shown in FIG. 1. Compound A showed significant synergistic anti-tumor efficacy with anti-CTLA-4 treatment in term of tumor volume.

The patterns of TILs in mice treated with combination of Compound A and anti-CTLA-4 antibody were measured. No specific patterns of TIL changes were found to be associated with the anti-tumor synergy between Compound A and anti-CTLA-4 antibody.

Previous studies in solid cancers suggested that tumors over-expressing PD-L1 may respond better to anti-PD1 therapy. PD-L1 or PD-L2 was transfected into the BNL-MEA cancer cell lines and clones that stably over-expressed PD-L1 or PD-L2 were selected. Over-expression of PD-L1 or PD-L2 did not influence the growth characteristics of the BNL-MEA cells significantly. Anti-PD-1 treatment suppressed the growth of PD-L1-overexpressing tumors more prominently.

5.2 5 Day SEB-Stimulated PBMC Assay

Figure 2A:
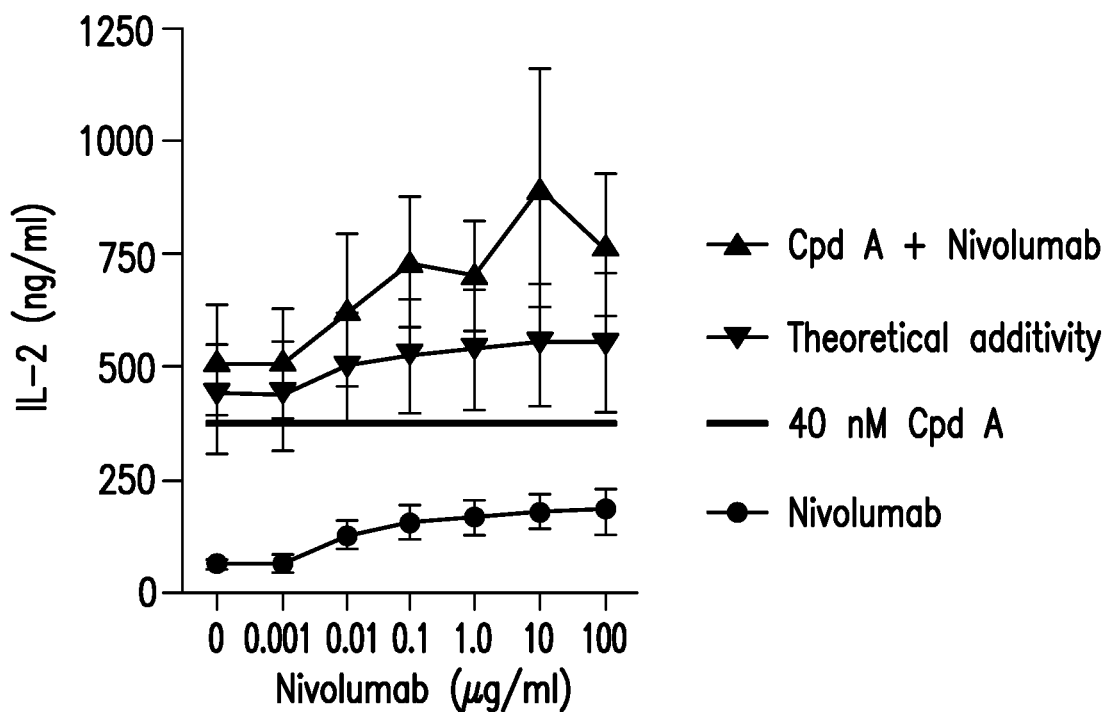
FIG. 2A shows the effects of combination of Compound A with nivolumab on IL-2 secretion in 5 day SEB-stimulated PBMC assay.
Figure 2B:
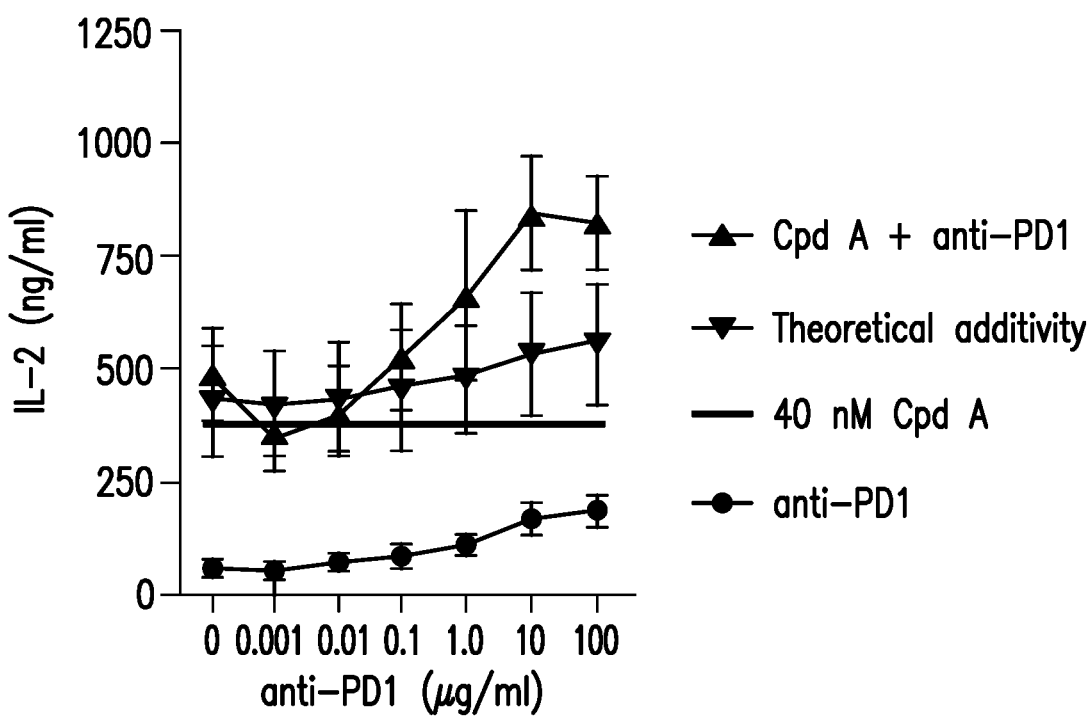
FIG. 2B shows the effects of combination of Compound A with an anti-PD-1 antibody on IL-2 secretion in 5 day SEB-stimulated PBMC assay.
Figure 2C:
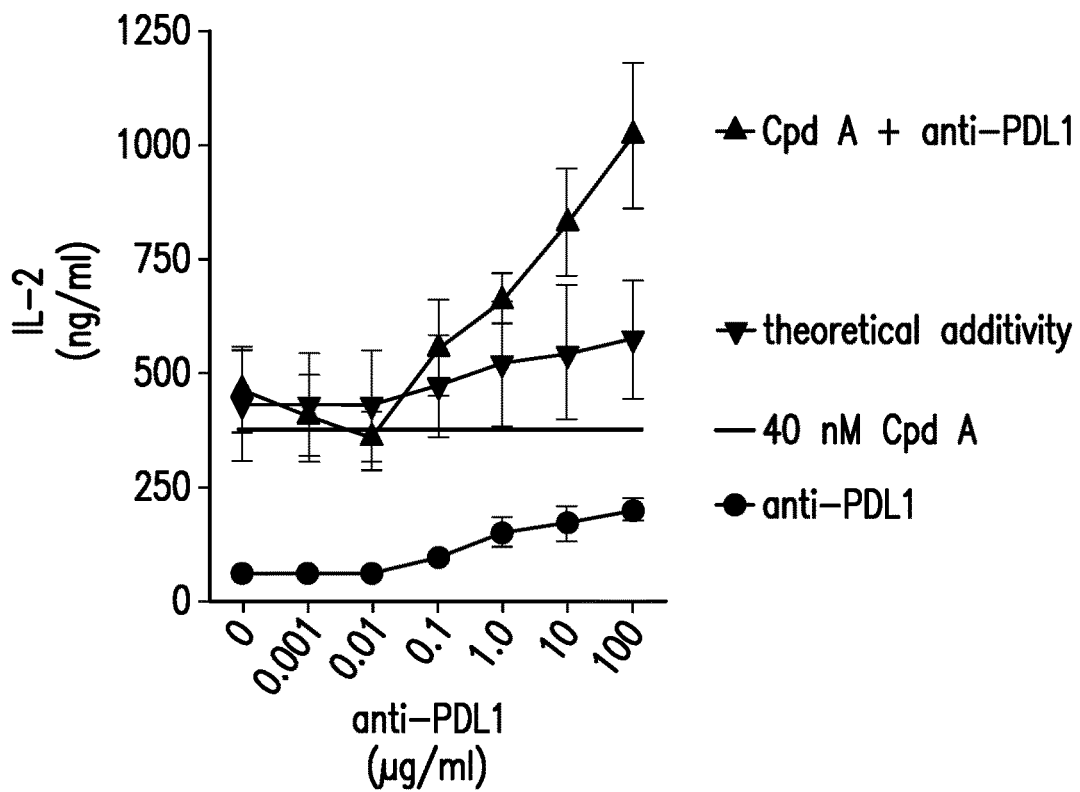
FIG. 2C shows the effects of combination of Compound A with an anti-PD-L1 antibody on IL-2 secretion in 5 day SEB-stimulated PBMC assay.

In one exemplary study, PBMC cells were pretreated with Compound A for 1 hour, then SEB/CPI were added for 5 days, IL-2 elisa on day 5. The results are shown in FIG. 2A (Compound A in combination with nivolumab), FIG. 2B (Compound A in combination with a surrogate commercial anti-PD-1 antibody from BioLegend), and FIG. 2C (Compound A in combination with a surrogate commercial anti-PD-L1 antibody from BioLegend). Compound A in combination with checkpoint inhibitors synergistically enhanced IL-2 secretion and activate T cells in vitro.

In another exemplary study, Compound A treated PBMCs from healthy donors were stimulated with 10 pg/ml of SEB (ThermoFisher Scientific) followed by addition of nivolumab (obtained from Blue Door Pharma), anti-PD1 (anti-human CD279 clone EH12.2H7, obtained from BioLegend, Cat #329926, lot B194623), and anti-PD-L1 (anti-human CD274 (B7-H1) clone 29E.2A3, obtained from BioLegend, Cat #329716, lot B197650) blocking antibodies. After 5 days of incubation, supernatants were collected and an ELISA for IL-2 (BD Biosciences) was utilized to examine secreted IL-2.

Figure 2D:
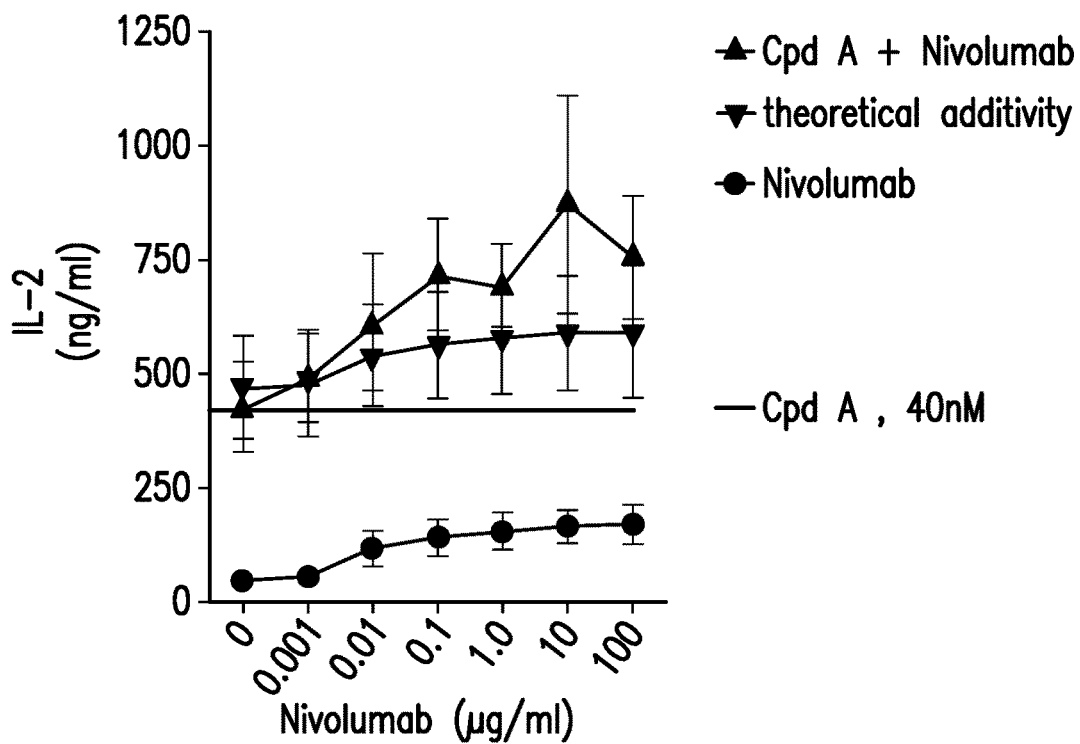
FIG. 2D shows the effects of combination of Compound A with nivolumab on IL-2 secretion in 5 day SEB-stimulated PBMC assay.
Figure 2E:
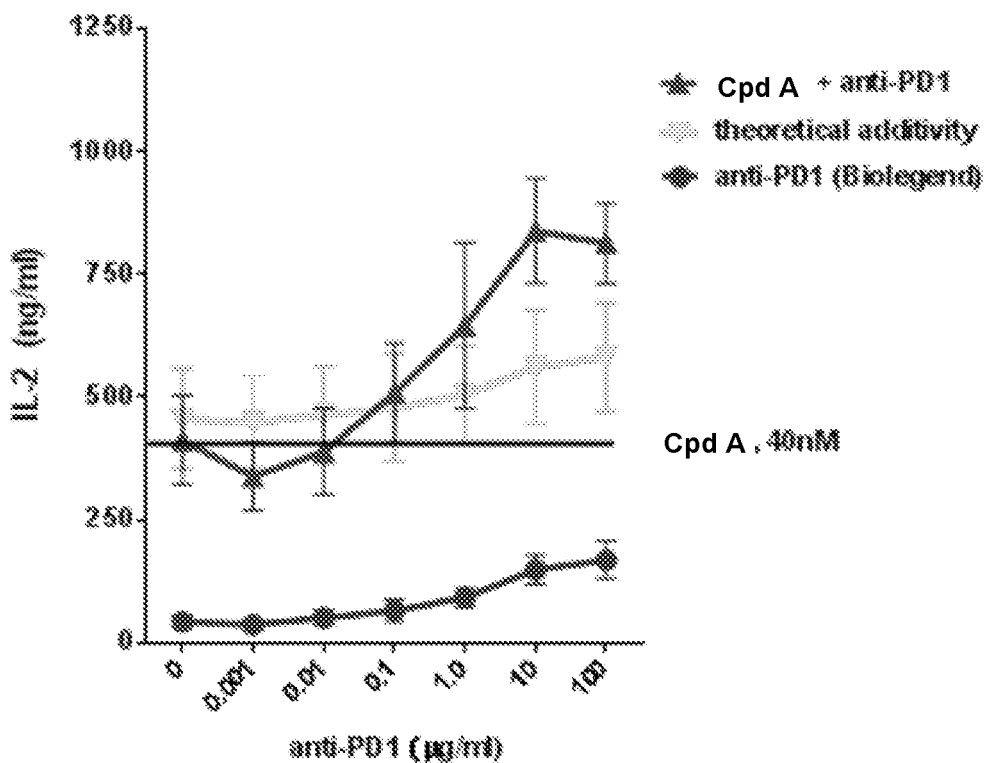
FIG. 2E shows the effects of combination of Compound A with an anti-PD-1 antibody on IL-2 secretion in 5 day SEB-stimulated PBMC assay.
Figure 2F:
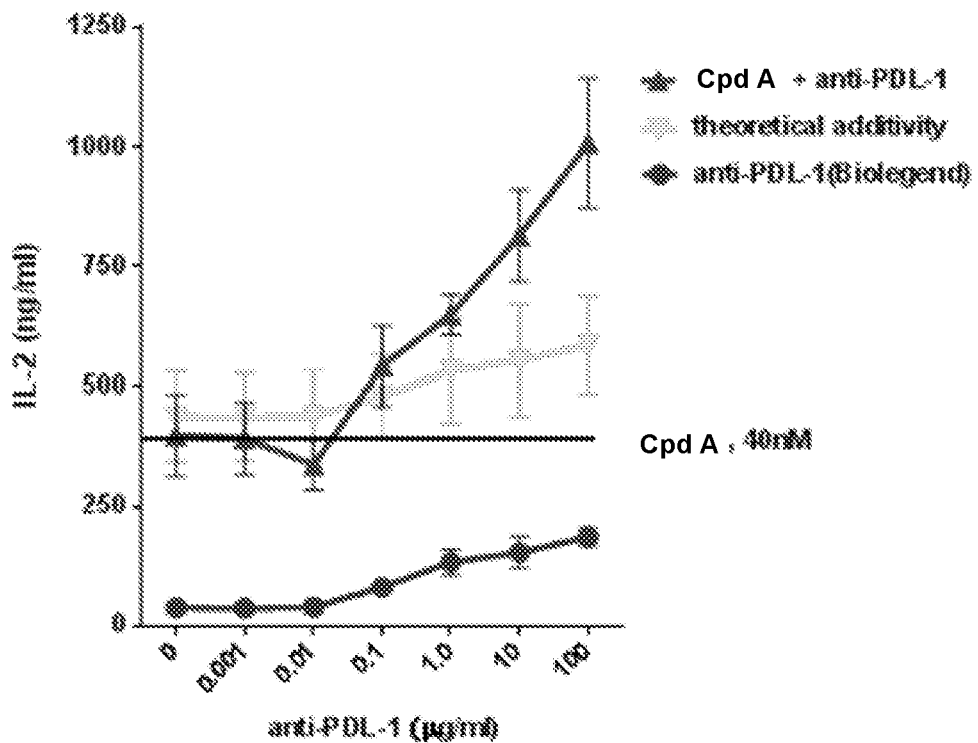
FIG. 2F shows the effects of combination of Compound A with an anti-PD-L1 antibody on IL-2 secretion in 5 day SEB-stimulated PBMC assay.

Combination of 40 nM Compound A with nivolumab (Nivo) titrated from 1 ng/ml to 100 μg/ml demonstrated synergistic IL-2 secretion compared to either single agent between 0.1-100 μg/ml nivolumab (FIG. 2D). Additionally, Compound A (40 nM) combined with 1 ng/ml to 100 μg/ml commercially available anti-PD-L1 or anti-PD-1 blocking antibodies demonstrated synergistic IL-2 secretion at concentrations above 1 μg/ml anti-PD-1 (FIG. 2E) or 10 μg/ml anti-PD-L1 antibodies (FIG. 2F).

5.3 Mixed Lymphocyte Reaction (MLR) Assay

Figure 3A:
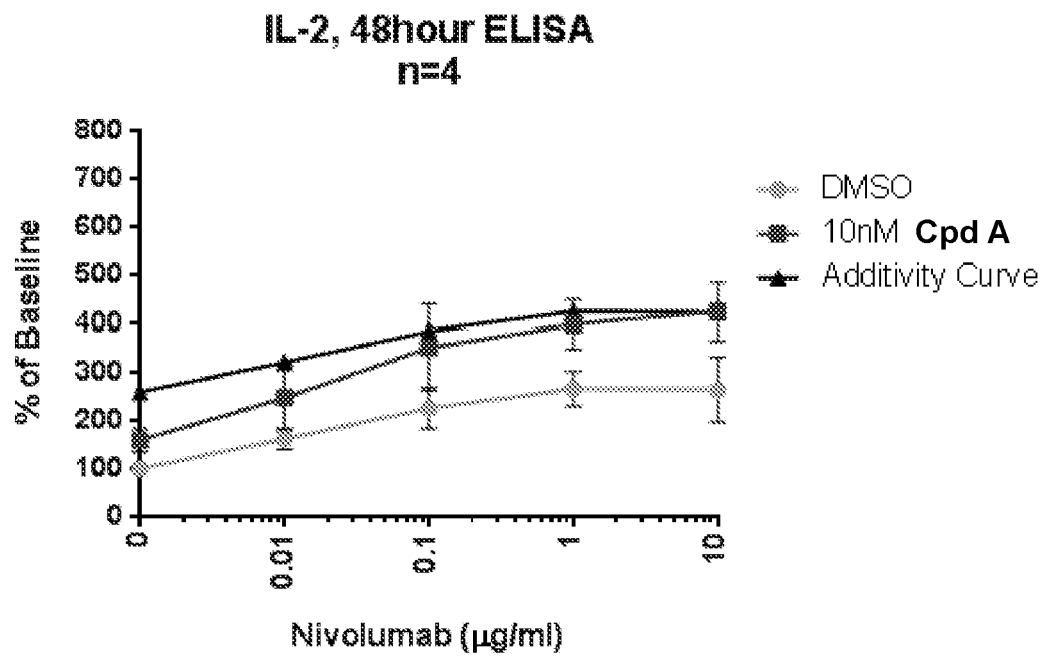
FIG. 3A shows the effects of combination of Compound A with nivolumab on IL-2 secretion in mixed lymphocyte reaction assay.
Figure 3B:
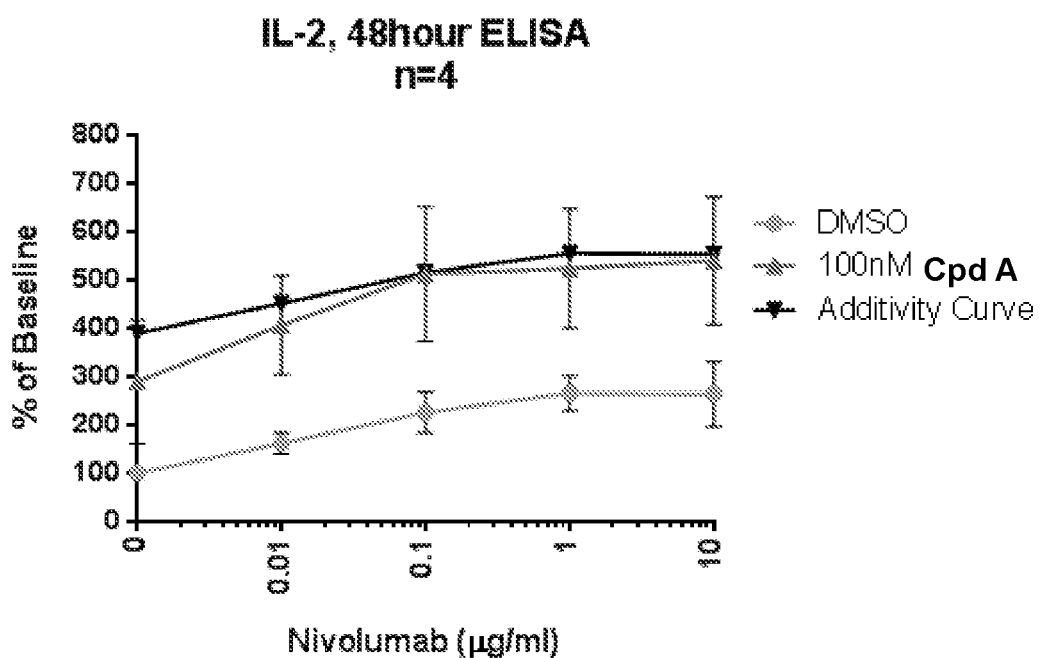
FIG. 3B shows the effects of combination of Compound A with nivolumab on IL-2 secretion in mixed lymphocyte reaction assay.
Figure 4A:
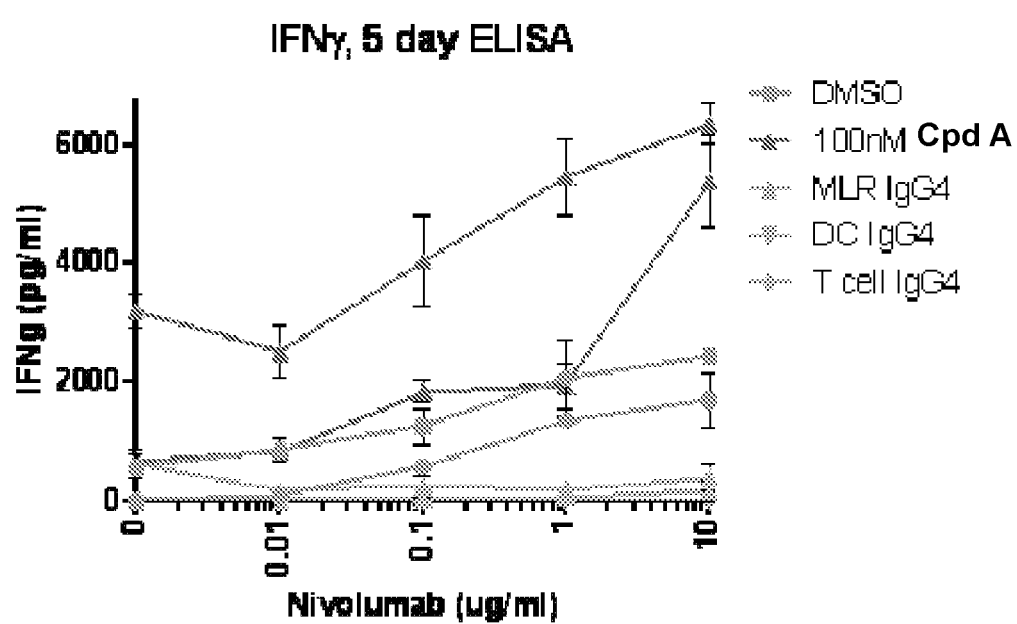
FIG. 4A shows the effects of combination of Compound A with nivolumab on IFNγ secretion in mixed lymphocyte reaction assay.

In one exemplary study, monocytes were isolated from buffy coat using Easy Sep kit (StemCell Technologies) and cultured in RPMI supplemented with 10% FBS, IL-4, and GM-CSF for 7 days. On day 7, CD4+ T cells were isolated from leukopak using Easy Sep kit (StemCell Technologies) and co-cultured with Monocyte-derived DC (MDC) using a 10:1 ratio. Secreted IL-2 was quantified by ELISA at 48 hours and IFNγ was measured at 5 days. Throughout the experiment, surface marker expression was determined by flow cytometry. The results are shown in FIG. 3A (IL-2, 10 nM Compound A), FIG. 3B (IL-2, 100 nM Compound A), and FIG. 4A (IFNγ, 100 nM). Compound A in combination with nivolumab enhanced IL-2 and IFNγ secretion in the mixed lymphocyte reaction.

In another exemplary study, monocytes were isolated from healthy donor buffy coat (Stem Cell Technologies) and cultured with 500 U/ml IL-4 and 250 U/ml GM-CSF (R&D Systems) for 7 days until the monocytes differentiated into dendritic cells (DC) by culturing with media containing a cocktail of IL-4 and GM-CSF for 7 days. On day 7, CD4+ T cells from a different healthy donor were isolated from a leukopak (Stem Cell Technologies). The DC and T cells were mixed at a ratio of 1:10 and co-cultured for 5 days with Compound A and nivolumab (obtained from Blue Door Pharma) or anti-PD-L1 (anti-human CD274 (B7-H1) clone 29E.2A3, obtained from BioLegend, Cat #329716, lot B197650). Supernatants were harvested for IL-2 ELISA at 48 hours (R&D Systems) and for IFNγ ELISA at 5 days (Thermo Fisher Scientific). Monocytes, DC, T cells, and mixed lymphocytes were stained for flow cytometric analysis of CD14, HLA-DR, CD80, CD86, CD83, CD40, CD3, PD-1, PD-L1 surface expression markers throughout the duration of the experiment.

Figure 3C:
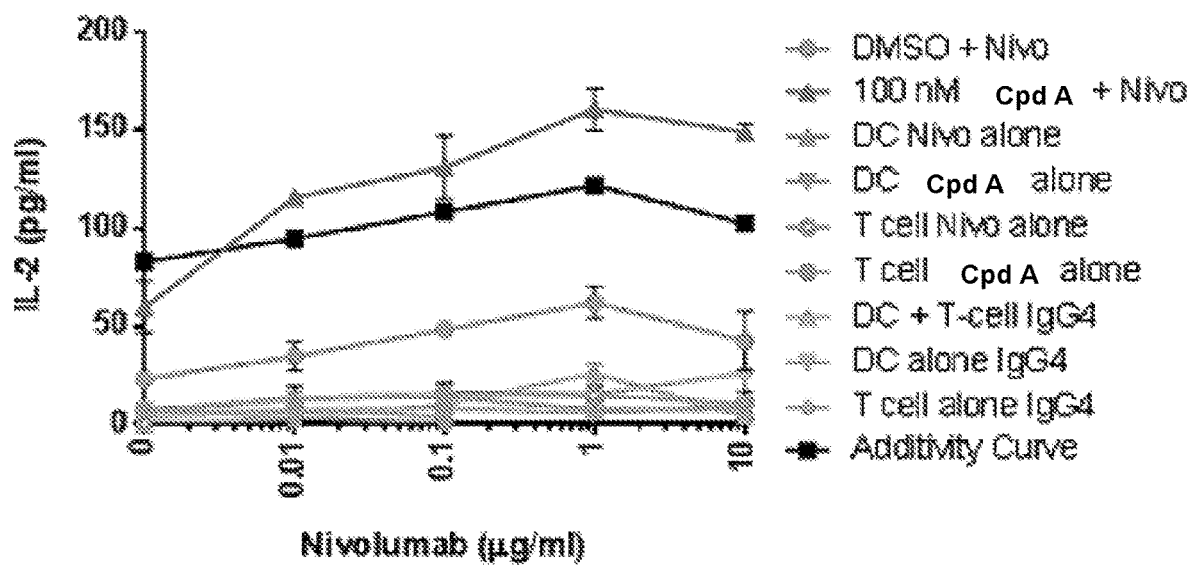
FIG. 3C shows the effects of combination of Compound A with nivolumab on IL-2 secretion in mixed lymphocyte reaction assay.
Figure 3D:
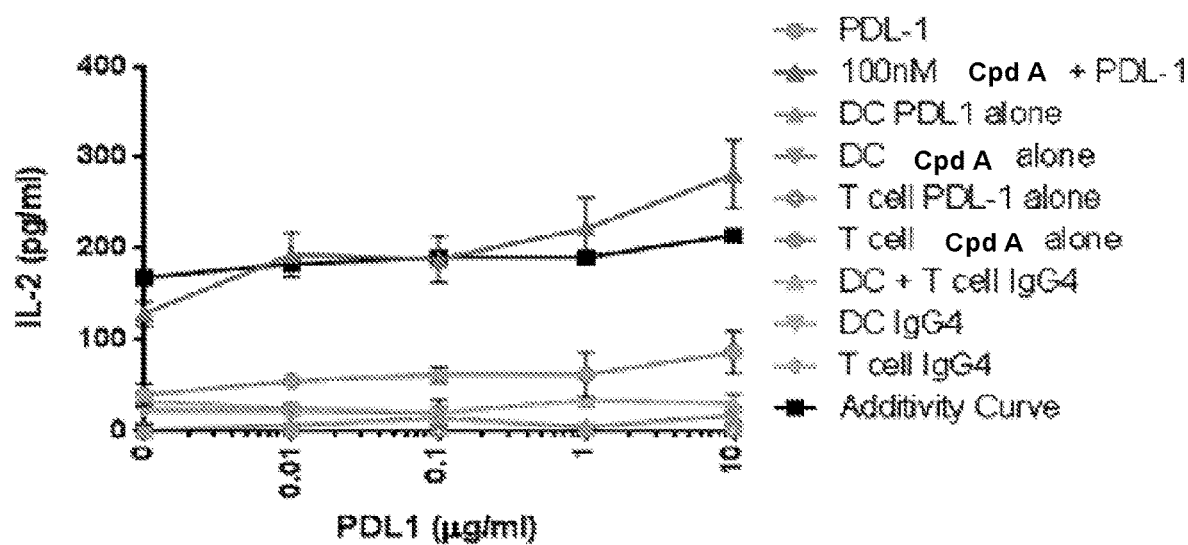
FIG. 3D shows the effects of combination of Compound A with an anti-PD-L1 antibody on IL-2 secretion in mixed lymphocyte reaction assay.
Figure 4B:
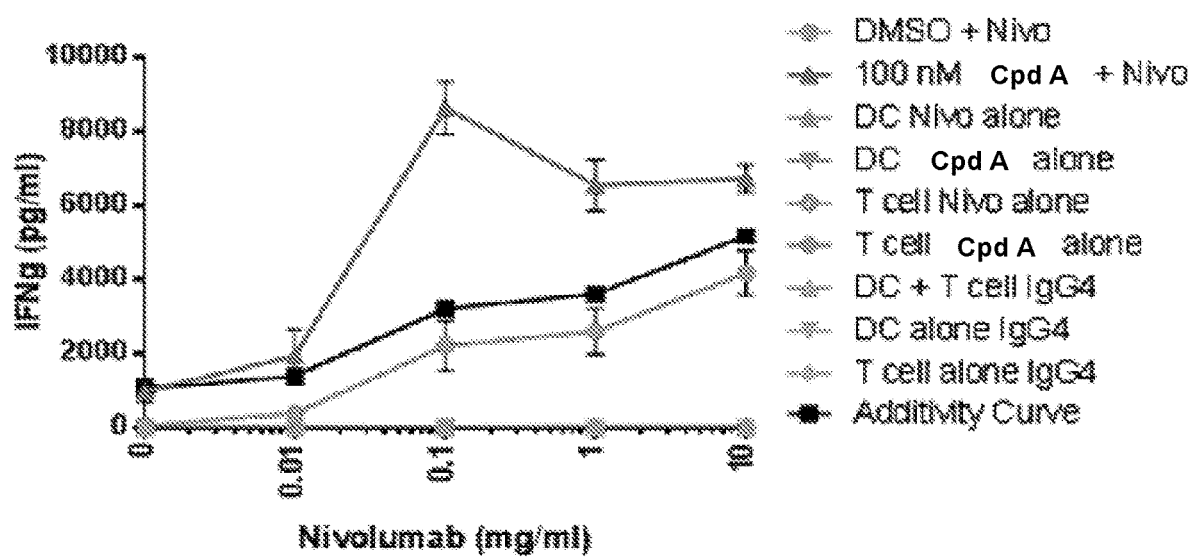
FIG. 4B shows the effects of combination of Compound A with nivolumab on IFNγ secretion in mixed lymphocyte reaction assay.
Figure 4C:
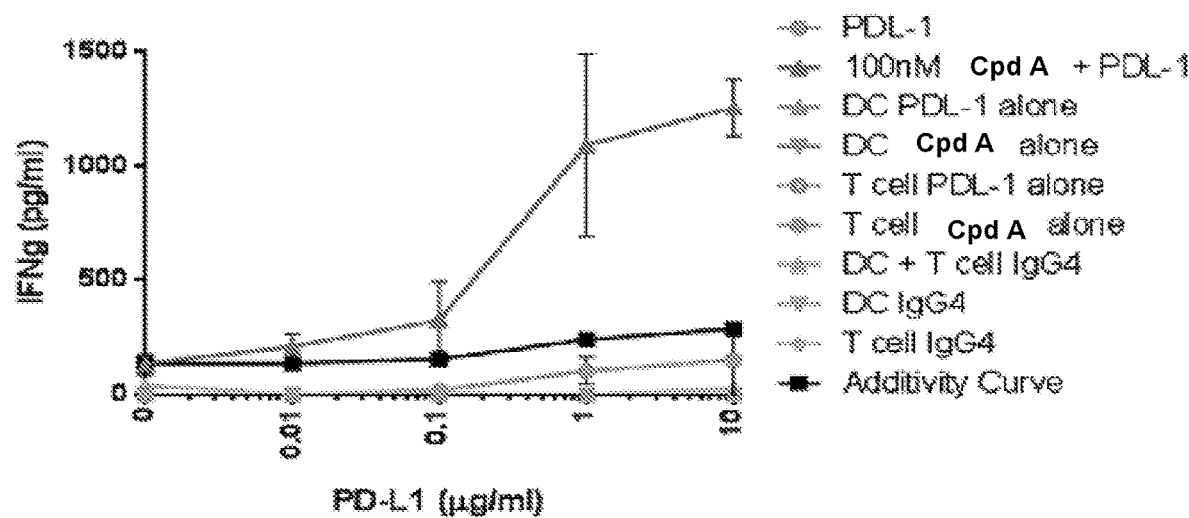
FIG. 4C shows the effects of combination of Compound A with an anti-PD-L1 antibody on IFNγ secretion in mixed lymphocyte reaction assay.

The combination of Compound A with nivolumab or anti-PDL-1 titrated from 0.01-10 μg/ml resulted in synergistic IL-2 secretion compared to either single agent at concentrations between 0.01-10 μg/ml for the nivolumab combination (FIG. 3C) and 1-10 μg/ml anti-PD-L1 (FIG. 3D). Additionally, IFNγ secretion increased synergistically with Compound A in combination with nivolumab between 0.1-10 μg/ml (FIG. 4B) or between 0.1-10 μg/ml anti-PD-L1 (FIG. 4C) after 5 days of co-culture. Theoretical additivity was calculated by summing the mean of each single agent treatment.

5.4 Lymphocyte Proliferation Assay

To further explore immune activation resulting from the combination of Compound A and nivolumab, proliferation of immune cell subsets including NK, NKT, CD4+ and CD8+ T cell was examined. CellTrace Violet (Thermo Fisher) labeled PBMCs from healthy volunteers were treated with Compound A and nivolumab in combination or as single agent, and stimulated with soluble anti-CD3/CD28 (Stem Cell Technologies) for 6 days. Cells were collected and flow cytometry was performed to assay for surface expression of CD3, CD4, CD8, and CD56 (BD Biosciences). Dead cells were excluded by live/dead fixable stain (ThermoFisher Scientific). Prior to flow cytometry, Count- Bright beads (Thermo Fisher Scientific) were added to examine changes in absolute cell count.

Figure 5A:
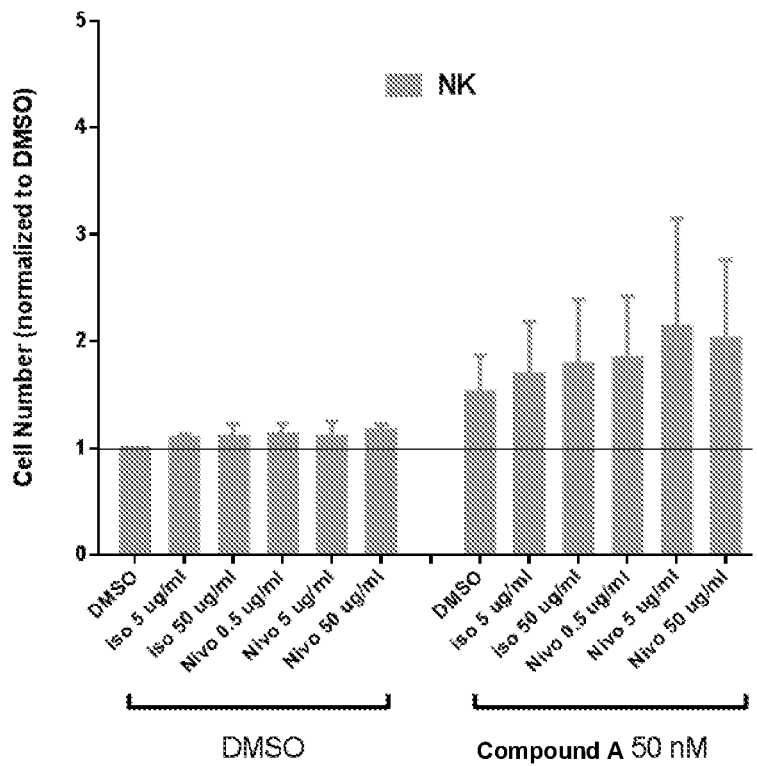
FIG. 5A shows the effects of combination of Compound A with nivolumab on proliferation in NK cells.
Figure 5B:
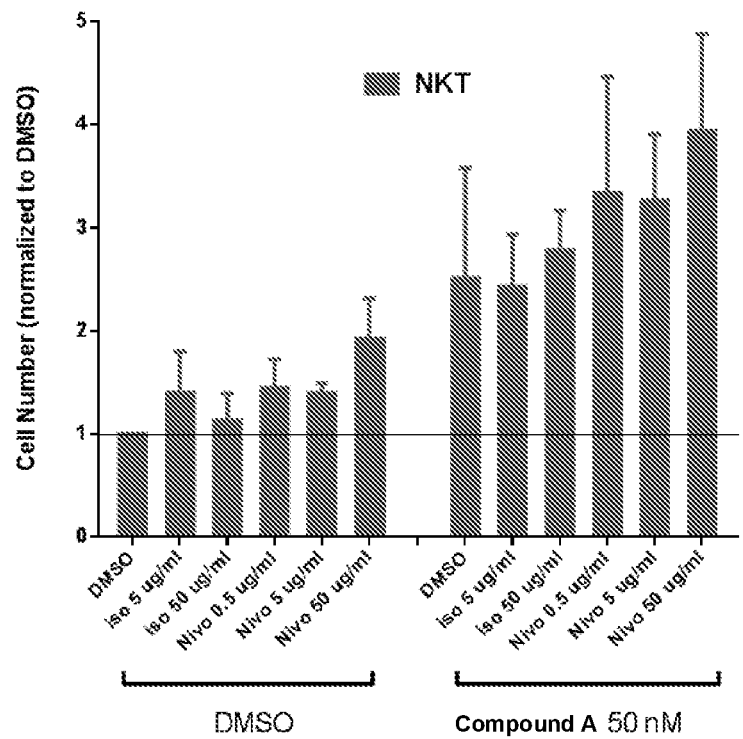
FIG. 5B shows the effects of combination of Compound A with nivolumab on proliferation in NKT cells.
Figure 5C:
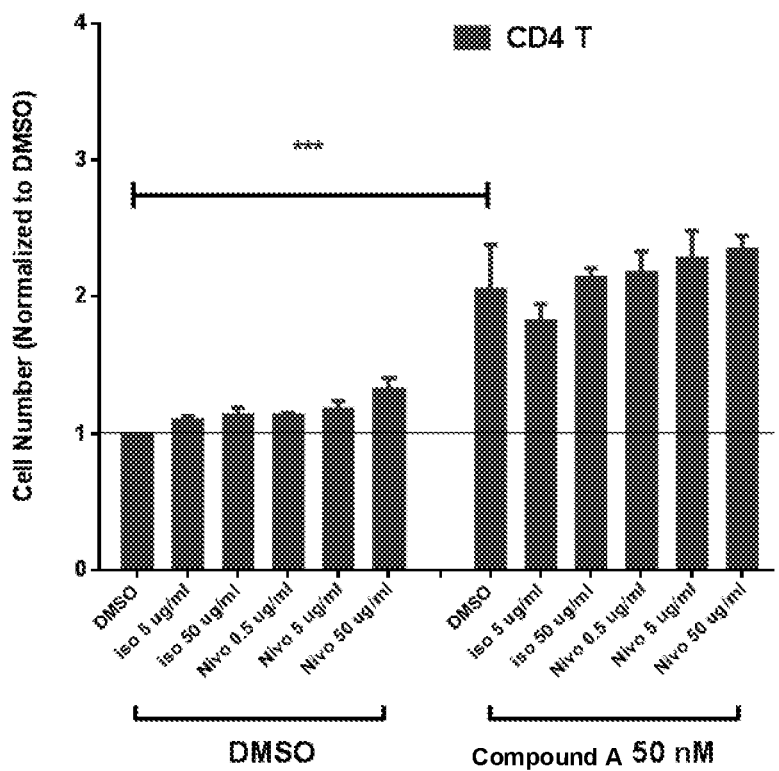
FIG. 5C shows the effects of combination of Compound A with nivolumab on proliferation in CD4+ T-cells.
Figure 5D:
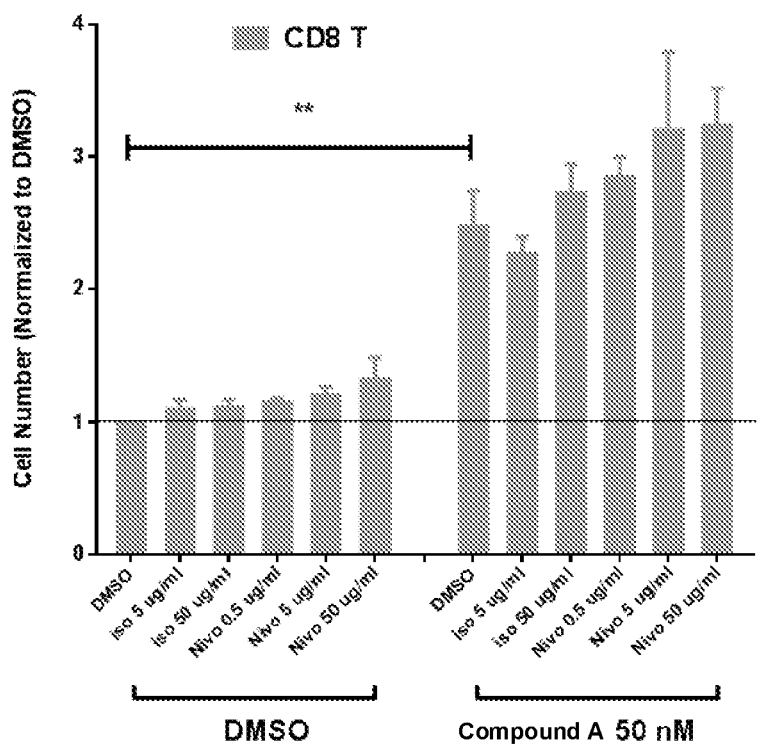
FIG. 5D shows the effects of combination of Compound A with nivolumab on proliferation in CD8+ T-cells.

Analysis of absolute cell numbers from flow cytometric profiles showed that the combination of Compound A with nivolumab enhanced proliferation in NK (FIG. 5A), NKT (FIG. 5B) and CD8+ T-cells (FIG. 5D), but not CD4+ T-cells (FIG. 5C).

5.5 PBMC Mediated Natural Cytotoxicity Against JHH4

The effect of Compound A plus checkpoint blockade on immune-mediated killing of HCC tumor cells is assessed in this study. PBMCs from healthy volunteers were stimulated with 10 pg/ml of SEB for 5 days. Target cells (JHH4, a PD-L1 positive HCC cell line) were labeled with CFSE (ThermoFisher Scientific) prior to co-culture with SEB-stimulated PBMCs treated with Compound A alone or in combination with immune checkpoint molecules. Four hours after co-culture, cells were washed and stained with Annexin V/ToPro-3 (ThermoFisher Scientific) prior to flow cytometry for analysis of apoptosis of HCC cells.

Figure 6:
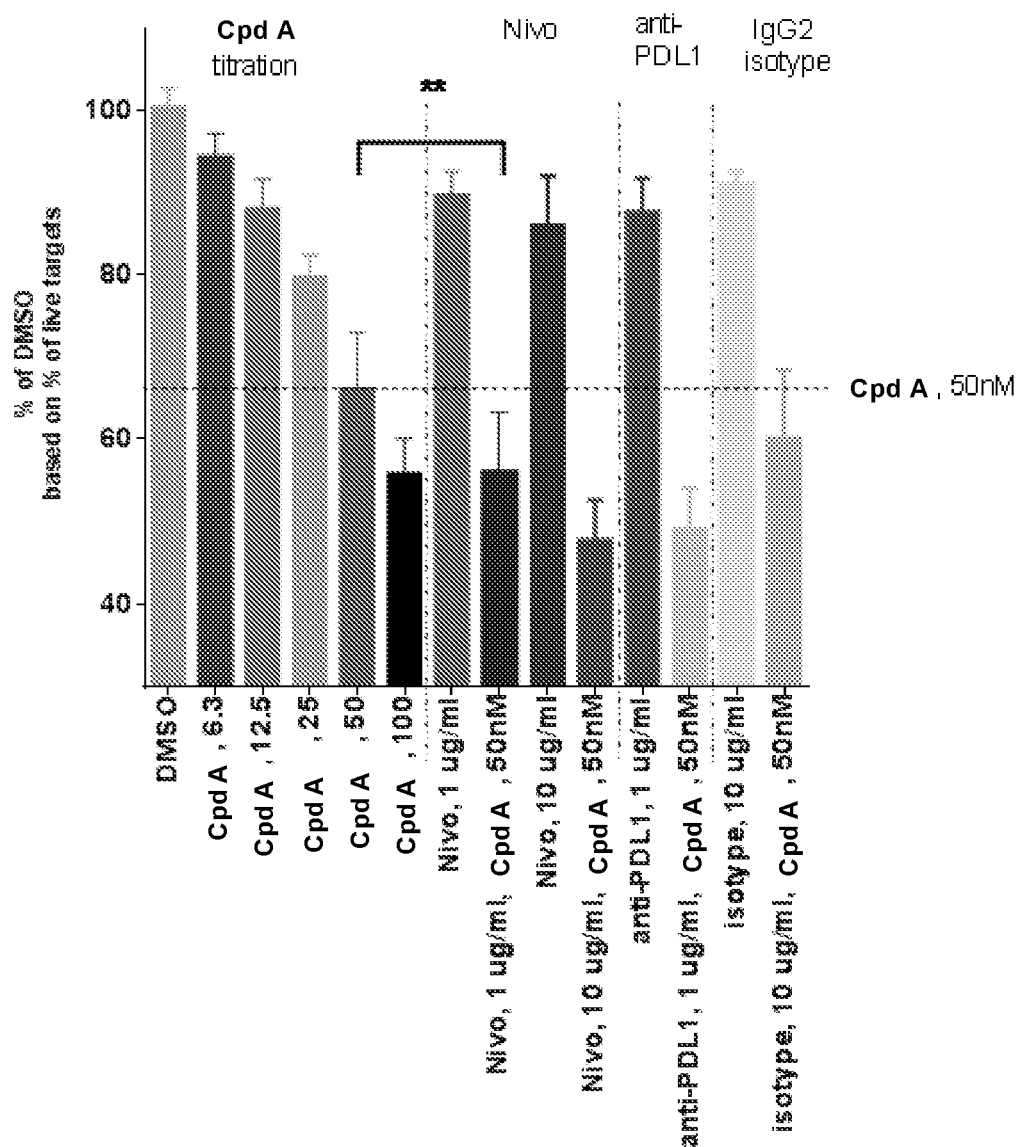
FIG. 6 shows the PBMC mediated natural cytotoxicity of combination of Compound A with nivolumab or anti-PD-L1 antibody against JHH4.

PBMC-mediated cell killing of HCC cell line JHH4 was significantly enhanced by treatment with 50 nM Compound A combined with 1-10 µg/ml nivolumab ($p<0.05$) or 1 µg/ml anti-PD-L1 ($p<0.05$) (FIG. 6).

5.6 Immunological Synapse Bioassay in CLL Cells

Immunological synapse bioassay was used to examine T cell interactions with target CLL tumor cells (modeling anti-tumor T cell responses in the tumor microenvironment (TME)) following Compound A treatment. The expression of co-signaling complexes at the immune synapse was measured.

Figure 7A:
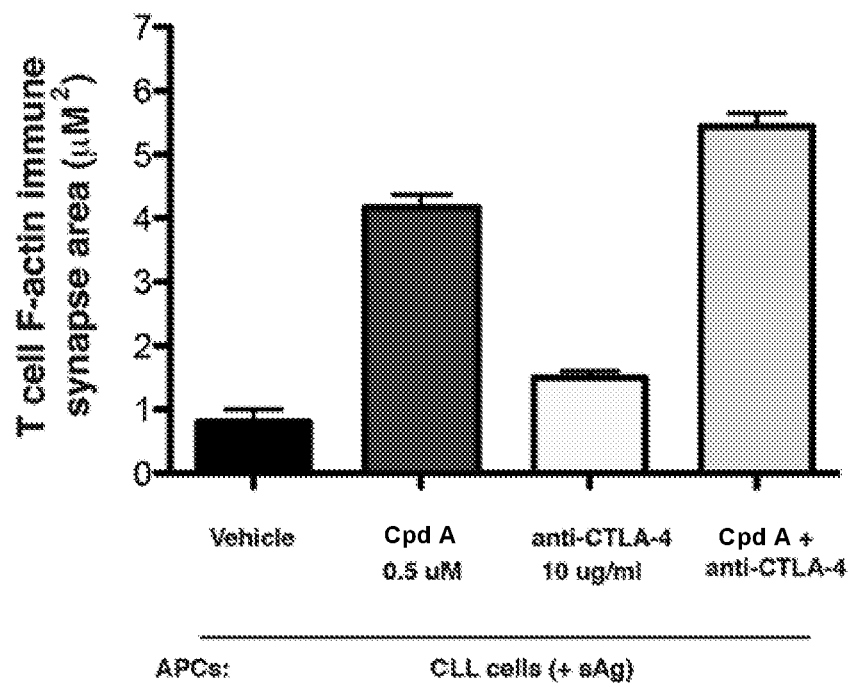
FIG. 7A shows the effects of combination of Compound A with anti-CTLA-4 antibody in immunological synapse bioassay in CLL cells.
Figure 7B:
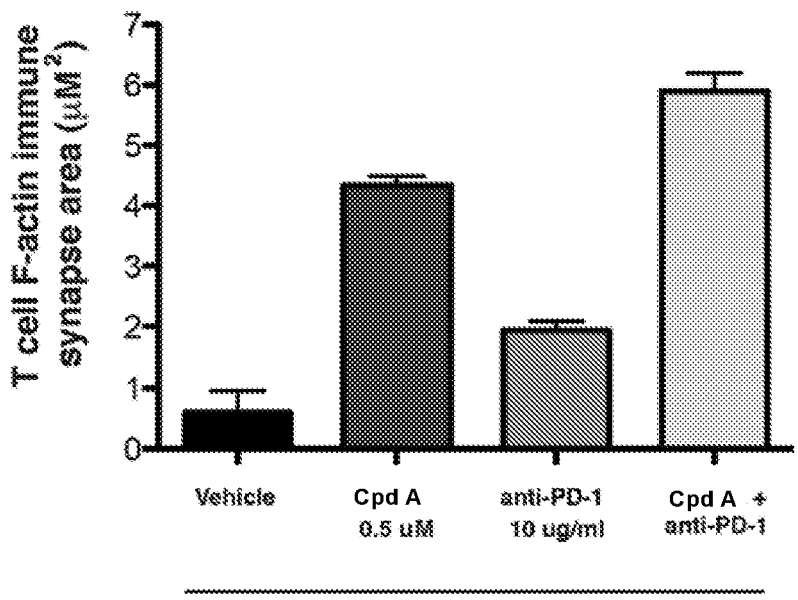
FIG. 7B shows the effects of combination of Compound A with anti-PD-1 antibody in immunological synapse bioassay in CLL cells.
Figure 7C:
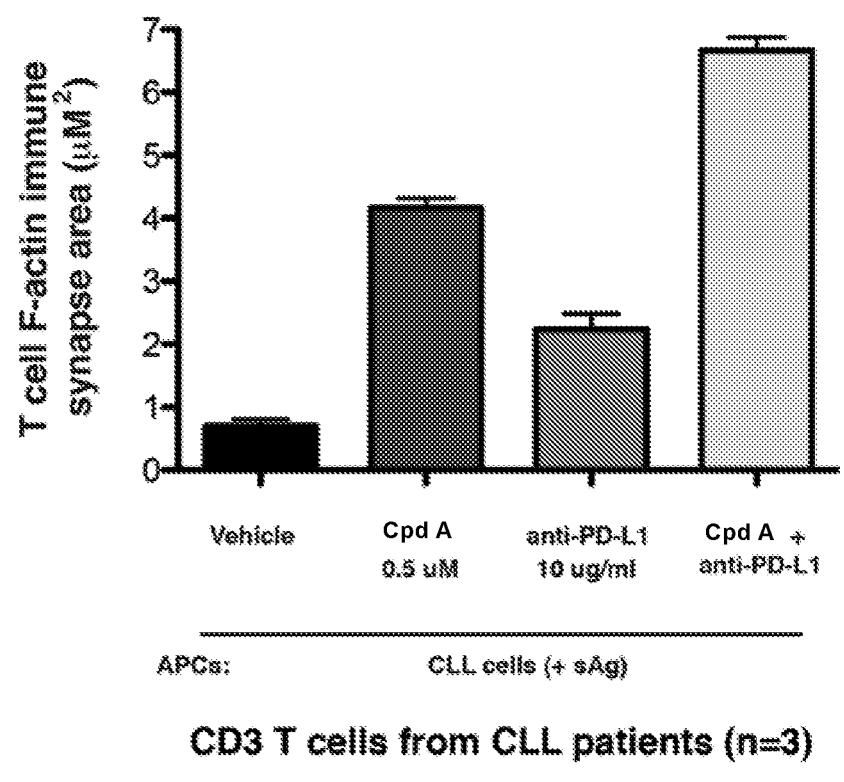
FIG. 7C shows the effects of combination of Compound A with anti-PD-L1 antibody in immunological synapse bioassay in CLL cells.

Results: Conjugation assays and confocal imaging were used to visualize intercellular conjugate interactions and F-actin polymerization at the immune synapse between $CD4^+$ and $CD8^+$ T cells and autologous CLL tumor cells pulsed with superantigen (acting as antigen-presenting cells, APCs). Peripheral blood was obtained from treatment naive CLL patients (n=40) that were representative of disease heterogeneity including stage and $IgV_H$ mutation status. Treatment of both purified CLL cells and $CD4^+$ or $CD8^+$ T cells with Compound A (0.01-1 µM for 24 h) dramatically enhanced the number of T cells recognizing tumor cells (% conjugation formation) and increased the formation of F-actin immune synapses (area size, $\mu m^2$) compared to vehicle treated cells ($P<0.01$). Notably, Compound A treatment induced T cells to engage in multiple tumor cell synapse interactions that were more pronounced in restored $CD8^+$ T cell lytic synapses. This immunomodulatory activity was detected across all CLL patient samples and drug concentrations tested. In addition, synapse strength as measured by total fluorescence intensity of F-actin per T cell:APC conjugate increased significantly with Compound A ($P<0.01$). This signaling data provides evidence that Compound A induces functional T cell synapses that control the assembly of signaling complexes between the T cell receptor (TCR) and the F-actin rich cytoskeletal layer. Following T cell recognition of APCs, co-signaling receptors co-localize at the immune synapse where they synergize with TCR signaling to promote (co-stimulatory receptors) or inhibit (co-inhibitory or 'immune checkpoint' receptors) T cell activation and effector functions. Quantitative image analysis studies revealed that restoration of T cell synapse activity with Compound A was accompanied by an increased recruitment of inducible co-stimulator (ICOS) to the synapse that was dose-dependent ($P<0.01$). Compound A treatment also increased polarized expression of CTLA-4 and PD-1 immune checkpoint proteins at the synapse with PD-L1+ tumor cells. The observed upregulation of co-inhibitory receptors led to combining Compound A with anti-CTLA-4 (FIG. 7A), anti-PD-1 (FIG. 7B), or anti-PD-L1 (FIG. 7C) blocking antibodies. Results show that the combinations increased T cell synapse activity compared to using these immunotherapies alone (p value).

The results show that Compound A can activate T cell immune synapse signaling against autologous CLL tumor cells. The results also show that Compound A's activation of T cells is associated with enhanced expression of the co-stimulatory receptor ICOS and co-inhibitory checkpoints CTLA-4 and PD-1 at the synapse site. The data demonstrates that this regulatory feedback inhibition can be utilized by the addition of anti-PD-L1, anti-PD-1 or anti-CTLA-4 immune checkpoint inhibitors to Compound A therapy to more optimally stimulateT cell activity against immunosuppressive tumor cells.

5.7 Clinical Trial (Lymphoma and Leukemia)

A Phase ½ open label multicenter study to assess efficacy, safety, and tolerability of combination therapies including Compound A and a checkpoint inhibitor in subjects with relapsed/refractory lymphoma or leukemia is performed.

The study will examine efficacy of combination therapies using Compound A and a checkpoint inhibitor for indications described herein. The study will be conducted in compliance with International Conference on Harmonisation (ICH) Good Clinical Practices (GCPs).

This is a multicenter, open label, Phase ½ study assessing the safety, tolerability, PK, Pd, and preliminary efficacy of durvalumab as given in combination with Compound A in select subtypes of leukemia including AML, CML, ALL, and CLL and subtypes of lymphoma including DLBCL, HL, FL, MCL, transformed large cell lymphoma, CLL/SLL, and MZL. The current study will include testing of combinational therapies in combination with other anti-cancer agents, including for example rituximab.

Rationale: Tumor-infiltrating lymphocytes (TILs) have the capacity to control the growth of many types of cancers. Most tumors show infiltration by TILs, but tumors modulate the local microenvironment through expression of inhibitory molecules. Without being bound by any particular theory, engagement of TIL cell-surface receptors with these inhibitory ligands likely leads to a dysfunctional immune response, causes T-cell exhaustion, and likely facilitates tumor progression. It is increasingly appreciated that cancers are recognized by the immune system, and under some circumstances, the immune system may control or even eliminate tumors. Novel monoclonal antibodies (mAbs) that block these inhibitory receptors have shown significant clinical activity across a number of tumor types.

Blockade of immune-checkpoint inhibitors such as cytotoxic T-lymphocyte-associated antigen 4 (CTLA-4), PD-1, and PD-L1 have shown clinical activity not only in conventionally immune-responsive tumors such as melanoma and renal cell carcinoma but also in non-small cell lung cancer and prostate cancer. Pembrolizumab and nivolumab are both PD-1 blocking antibodies and the first in the anti-PD-1 pathway family of checkpoint inhibitors to gain approval from the US Food and Drug Administration (FDA), pembrolizumab for melanoma and nivolumab for melanoma and squamous non-small cell lung cancer. Both pembrolizumab and nivolumab have received European Commission regulatory approval for the treatment of metastatic melanoma. The European Commission has also approved nivolumab for the treatment of advanced previously treated squamous NSCLC. Nivolumab has gained approval for the treatment of melanoma in Japan.

Lymphomas and leukemias comprise multiple histologies. It is hypothesized without being bound by any particular theory that checkpoint inhibitors such as durvalumab have activity in multiple indications based on known expression pattern of PD-L1/PD-1, available preclinical data, and recent clinical data utilizing nivolumab or pembrolizumab in relapsed refractory classical Hodgkin lymphoma and promising early data of pidilizumab alone or in combination with rituximab in diffuse large B-cell lymphoma (DLBCL) or follicular lymphoma (FL), respectively; also nivolumab monotherapy has shown antitumor activity in DLBCL, FL and T-cell lymphomas.

The programmed cell death-1 (PD-1) plays an important role in the regulation of the immune response. The PD-1 receptor, in conjunction with receptor ligands PD-L1 and PD-L2, functions to regulate the immune system primarily by down regulating signals of the T-cell receptor. PD-L1 expressed on tumor cells binds to PD-1 on T-cells which leads to down-regulation of T-cell activity and allows tumor cells to evade the immune response.

Based on in vitro studies, an antibody that blocks the interaction between PD-L1 and its receptors can relieve PD-L1-dependent immunosuppressive effects and enhance the cytotoxic activity of antitumor T-cells. The levels of tumor-infiltrating lymphocytes, and more specifically cytotoxic T-cells, have been correlated with improved prognosis in a number of cancers including colorectal, melanoma, and lung. Based on these findings, an anti-PD-L1 antibody could be used therapeutically to enhance antitumor immune responses in multiple forms of cancer.

Treatment Period. Subjects begin treatment following confirmation of eligibility. For all subsequent visits, an administrative window of ±2 days for study Day 1 visits and ±1 for scheduled interim study visits (e.g., Day 18, 15, 22 visits) are allowed. Subjects who receive Compound A should have at least a 7-day rest between two 21-day treatment periods and therefore this should be taken into consideration when applying the visit window of ±2 days. If assessments are performed within 48 hours of Day 1 of each cycle, safety laboratory and physical examinations need not be repeated on Day 1. Treatment cycles are 28 days in duration. The following evaluations are performed:
Adverse event assessment/adverse events of special interest (including SPM).
Concomitant medications/procedures evaluation.
Physical examination including evaluation of lymph nodes, spleen and liver are performed. Documentation of any enlargement of the lymph nodes, spleen and/or liver should be recorded in the source document and CRF.
Body weight are measured.
Body surface area (as required per the site's local practice for rituximab or bendamustine).
Vital signs include blood pressure, pulse, and body temperature.
ECOG Performance Status are scored.
End of Treatment. An end of treatment (EOT) evaluation are performed for subjects who are withdrawn from treatment for any reason as soon as possible after the decision to permanently discontinue treatment has been made. The following evaluations are performed:
Adverse event assessment/adverse events of special interest (including SPM).
Concomitant medications/procedures evaluation.
Physical examination including evaluation of lymph nodes, spleen and liver are performed. Documentation of any enlargement of the lymph nodes, spleen and/or liver should be recorded in the source document and CRF.
Body weight are measured.
Vital signs include blood pressure, pulse, and body temperature.
ECOG Performance Status are scored.
12-lead electrocardiogram are recorded.

Efficacy Assessments. For lymphoma, disease response to treatment is determined by the Lugano Classification including a careful review of imaging and laboratory studies and clinical findings. Integrated PET-CT is preferred for response assessment of FDG-avid lymphomas (e.g., DLBCL, HL, FL, MCL, transformed large cell lymphoma), while dedicated CT scan alone is preferred for FDG non-avid and variably FDG-avid histologies (e.g., CLL/SLL, MZL).

Minimal Residual Disease (Immunophenotyping of Blood for Circulating CLL Cells by Multiparameter Flow Cytometry) (CLL) If CBC with differential demonstrates the normalization of WBC to normal limits and no evidence of lymphocytosis, peripheral blood sample is obtained (within 14 days) to determine the MRD status of the CLL in peripheral blood by multiparameter flow cytometry. In one section of the study, subjects receive:
Durvalumab (IV) infusion on Day 1 of Cycles 1 through 13 (i.e., 12 months);
Compound A (PO) once daily on Days 1 to 21(inclusive) of: Cycles 1 through 13 in indolent NHL (i.e., FL or MZL) or Until disease progression, unacceptable toxicity, or discontinuation for any other reason in aggressive NHL (e.g., DLBCL); and
Rituximab (IV) infusion on Days 2, 8, 15 and 22 of Cycle 1 and on Day 1 from Cycles 2 through 5.

All treatment cycles are 28 days. Durvalumab infusion is administered before any other IP on the days which more than one investigational treatment should be given (e.g., Day 1 of Cycles 1 through 13), and then Compound A administration and rituximab infusion are recommended to follow, respectively.

Initial cohorts of 3 subjects are treated at varying dose levels. If one DLT occurs in the first 3-subject cohort at a dose level during the DLT observation period (i.e., from the time of the first IP dose through completion of Cycle 2), that cohort enrolls up to 6 subjects. Even in the absence of a DLT, additional subjects may be evaluated within a dose cohort if recommended by the SRC to adequately evaluate the safety or treatment effects of durvalumab in combination with Compound A and/or rituximab (depending on dose level). If dose level 1 is found to be the NTD, the next dose level may be explored.

TABLE 1

Dose Finding: Arm A Dose Levels

| Dose Level | Durvalumab (mg) | Compound A (mg) | Rituximab (mg/m2) |
|---|---|---|---|
| −1B | 1500 | 10 | 375 |
| −1A | 1500 | 10 | — |

TABLE 1-continued

Dose Finding: Arm A Dose Levels

| Dose Level | Durvalumab (mg) | Compound A (mg) | Rituximab (mg/m2) |
|---|---|---|---|
| 1 (Starting) | 1500 | 20 | — |
| 2 | 1500 | 20 | 375 |
| Schedule (28 day cycle) | D 1 of Cycles 1-13 | Once daily on days 1-21 Up to 12 months in FL or MZL Up to disease progression in aggressive histologies | Weekly in Cycle 1 (days 2, 8, 15, 22) and Day 1 of cycles 2-5 |

Efficacy Analysis. In the dose confirmation part and dose expansion part, treatment efficacy is evaluated by different histology cohorts for each treatment arm. Efficacy analysis is performed for particular treatment arm and subject histology cohort by combining data from both dose confirmation part and dose expansion part. Efficacy analysis is also be performed separately for dose confirmation part and dose expansion part as well.

For lymphoma subjects, response evaluation is based on IWG Response Criteria for Malignant Lymphoma (the Lugano Classification) (Cheson 2014). The overall response rate (ORR) is defined as the percent of subjects with best response of CR or PR. Duration of response (DoR) is defined for responders only as the time from the first response (CR or PR) to. For CLL subjects, response evaluation is based on IWCLL guidelines for diagnosis and treatment of CLL (Hallek, 2008), as modified by (Hallek, 2012) and (Hallek, 2013). The overall response rate (ORR) is defined as the percent of subjects with best response of CR, CRi, nPR, PR, or PRL. Duration of response (DoR) is defined for responders only as the time from the first response (CR, CRi, nPR, PR, or PRL) to disease progression or death.

The response rate based on the best response during durvalumab treatment as well as during entire efficacy evaluation period are summarized by subject histology cohort for each treatment arm.

For subjects with response, duration of response is censored at the last date that the subject was known to be progression free. Duration of response is analyzed using the Kaplan-Meier method. Median duration of response along with two-sided confidence interval are provided for each treatment arm and subject histology cohort.

Progression-free survival (PFS) is calculated as the time from first IP dose to the first documented progression or death due to any cause during the entire efficacy evaluation period. Median PFS including 2-sided 95% CL is provided for each histology cohort within the same treatment arm.

Safety Analysis. Safety analysis includes all subjects in the Safety population. Investigational product exposure is summarized for each treatment arm and histology cohort including duration of investigational product, total dose taken, and dose reductions. Adverse events, vital sign measurements, clinical laboratory measurements, physical examination and concomitant medications are summarized by treatment arm and histology cohort.

Adverse events are coded according to Medical Dictionary for Drug Regulatory Activities (MedDRA) and classified using the NCI CTCAE. The incidence rates of AEs are tabulated by system organ class and preferred term. The incidence of AEs also is tabulated by severity within each system organ class and preferred term. The most severe grade of each preferred terms and adverse events of special interest for a subject are utilized for summaries of AEs by NCI CTCAE grade. Subsets of AEs to be summarized include AESIs, SAES, suspected treatment-related AEs, and AEs that resulted in withdrawal of investigational product.

All AEs with corresponding attributes are displayed in a by-subject listing. AEs leading to death or to discontinuation from treatment, events classified as NCI CTCAE grade 3 or higher, suspected treatment-related events, and SAES also are displayed in separate by-subject listings.

Laboratory data are graded according to NCI CTCAE severity grade. The frequencies of the worst severity grade observed during treatment are displayed in cross-tabulations by baseline status for each treatment arm and histology cohort. For variables for which an NCI CTCAE scale does not exist, the frequency of subjects with values below, within, and above the normal ranges pretreatment and during treatment is summarized by treatment and histology cohort. Change from baseline is descriptively summarized at each post-baseline visit by treatment arm and histology cohort.

5.8 Clinical Trial (HCC)

A phase ½, multicenter, open-label, dose finding study to assess the safety, tolerability, and preliminary efficacy of Compound A in combination with nivolumab in subjects with unresectable hepatocellular carcinoma (HCC) is performed.

This study is a Phase ½ dose escalation and expansion clinical study of Compound A in combination with nivolumab in subjects with unresectable hepatocellular carcinoma (HCC) who have progressed after or were intolerant to no more than 2 previous systemic therapies for unresectable HCC, or are naïve to systemic therapy.

Subjects have received either none or no more than 2 previous systemic therapies. The dose escalation part of the study explores 1 or more dose levels of Compound A in combination with nivolumab using a modified dose escalation (3+3) design, followed by an expansion part once the recommended Phase 2 dose (RP2D) is defined.

The study is designed to explore two dose levels, to identify the RP2D, and is not required to escalate to a nontolerated dose (NTD) or Maximum tolerated dose (MTD). Compound A initially is administered orally 5 consecutive days out of 7 (5 days on/2 days off weekly) on Days 1 to 5, 8 to 12, 15 to 19 and 22 to 26 of each 28-day cycle. The investigated starting daily dose of Compound A is 2.0 mg, and one subsequent dose level (4.0 mg) is planned to be evaluated based on evaluation of pre-specified Dose limiting toxicity (DLTs). The study intends to identify the RP2D at or below the 4.0 mg dose level, however intermediate dose levels, or a higher dose level, may be evaluated at the discretion of the Safety Review Committee (SRC). Dose escalation to the intermediate or higher dose levels of Compound A does not exceed 50% of the previously established tolerable dose level. Smaller dose increments based on toxicity, pharmacokinetics (PK) profile and PD findings may be evaluated, if necessary. Nivolumab is administered at the dose of 3.0 mg/kg intravenously (IV) every 2 weeks. Once the RP2D for dosing of Compound A in combination with nivolumab is defined, expansion (Phase 2) starts.

A modified 3+3 dose escalation design is used to identify the initial toxicity of the combination. Up to six subjects are concurrently enrolled into a dose level. Decisions as to which dose level to enroll a new subject is based on the number of subjects enrolled and evaluable, the number of subjects experiencing DLTs, and the number of subjects enrolled but who are not yet evaluable for toxicity in the current cohort at the time of new subject entry.

A dose may be considered an Nontolerated dose (NTD) if 2 or more out of up to 6 evaluable subjects in a cohort experience a DLT in Cycle 1. During dose escalation, the decision to either evaluate a higher dose level, an intermediate dose level, or declare the RP2D dose (or if applicable, NTD) is determined by the Safety review committee (SRC), based on their review of all available clinical data, PK, Pharmacodynamic (PD) and laboratory safety data for a given dose cohort.

The composition of the SRC is defined in the SRC charter and includes at least all the primary investigators (PIs) of active sites and the medical monitors and safety physician.

Non-evaluable subjects are replaced at the discretion of the SRC.

Following completion of the dose escalation part (Phase 1), up to 30 additional subjects are enrolled in an expansion part (Phase 2). A futility analysis is conducted as follows. In the first 14 subjects treated, if no responder is observed out of 14 subjects then enrollment for the expansion cohort stops for futility. Enrollment continues during the evaluation of the 14 subjects. If ≥1 subject out of 14 responds (Complete Response (CR) or Partial response (PR)), then approximately 30 total subjects are enrolled in the Phase 2 portion. The SRC continues to review safety data regularly throughout the study and makes recommendations about study continuation and dose modification, as appropriate.

Primary Outcome Measures: The combined incidence of complete response (CR)+partial response (PR), by investigator assessment of response by Response Evaluation Criteria in Solid Tumors (RECIST) 1.1.

Arm Description: Compound A orally 5/7 days starting at 2.0 mg with nivolumab Intravenously (IV) 3 mg/kg every 2 weeks. Cohorts of up to 6 subjects per dose level until Recommended Phase 2 dose (RP2D).

Arm Description: Compound A orally 5/7 days at Recommended Phase 2 dose (RP2D) and nivolumab Intravenously (IV) 3 mg/kg every 2 weeks.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of treating or managing a hematological cancer or solid tumor comprising administering to a patient in need thereof a therapeutically effective amount of Compound A of following formula, or a pharmaceutically acceptable salt or solvate thereof:

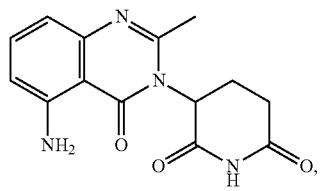 [SMILES: Cc1nc2cccc(N)c2c(=O)n1C1CCC(=O)NC1=O]

in combination with a therapeutically effective amount of one or more checkpoint inhibitor(s) selected from an anti-CTLA-4 antibody, an anti-PD-1 antibody and an anti-PD-L1 antibody.

2. The method of claim 1, which is a method of treating or managing a hematological cancer.

3. The method of claim 2, wherein the hematological cancer is acute myeloid leukemia (AML), acute lymphocytic leukemia (ALL), adult T-cell leukemia, chronic lymphocytic leukemia (CLL), hairy cell leukemia, myeloproliferative disorder, chronic myelogenous leukemia (CML), human lymphotropic virus-type 1 (HTLV-1) leukemia, or B-cell acute lymphoblastic leukemia.

4. The method of claim 3, wherein the hematological cancer is CLL.

5. The method of claim 3, wherein the hematological cancer is AML.

6. The method of claim 3, wherein the hematological cancer is ALL.

7. The method of claim 2, wherein the hematological cancer is Hodgkin lymphoma (HL) or non-Hodgkin lymphoma (NHL).

8. The method of claim 7, wherein the hematological cancer is NHL.

9. The method of claim 1, which is a method of treating or managing a solid tumor.

10. The method of claim 9, wherein the solid tumor is a sarcoma.

11. The method of claim 9, wherein the solid tumor is liver cancer, pancreatic cancer, renal cell cancer, lung cancer, skin cancer, thyroid cancer, brain tumor, colorectal cancer, bladder cancer, breast cancer, ovarian cancer, or head or neck cancer.

12. The method of claim 9, wherein the solid tumor is glioma, glioblastoma, primary ductal carcinoma, lung carcinoma, colon adenocarcinoma, colorectal carcinoma, hepatocellular carcinoma (HCC), colorectal adenocarcinoma, neuroendocrine tumors, Kaposi's sarcoma, non-small cell lung cancer, small cell lung cancer, melanoma or soft tissue sarcoma.

13. The method of claim 9, wherein the solid tumor is HCC.

14. The method of claim 13, wherein the checkpoint inhibitor is nivolumab.

15. The method of claim 14, wherein Compound A, or a pharmaceutically acceptable salt or solvate thereof, is administered once daily for 5 consecutive days followed by 2 days of no administration in one or more 7 days cycles, and nivolumab is administered once every 2 weeks.

16. The method of claim 15, wherein Compound A, or a pharmaceutically acceptable salt or solvate thereof, is administered at a dose of about 2 mg once daily for 5 consecutive days followed by 2 days of no administration in one or more 7 days cycles, and nivolumab is administered at a dose of about 3 mg/kg once every 2 weeks.

17. The method of claim 13, wherein the HCC is unresectable HCC.

18. The method of claim 1, wherein the hematological cancer or solid tumor is newly diagnosed, relapsed, refractory, or relapsed and refractory.

19. The method of claim 1, wherein the patient has received no prior therapy for the hematological cancer or solid tumor.

20. The method of claim 1, wherein the patient has received one, two, three, or more prior therapies for the hematological cancer or solid tumor.

21. The method of claim 20, wherein the patient has demonstrated progression or intolerance on one, two, three, or more prior therapies.

22. The method of claim 1, wherein the patient has minimal residual disease (MRD) after receiving a prior therapy.

23. The method of claim 22, wherein the level of minimal MRD in the patient is higher than a reference level.

24. The method of claim 22, wherein the level of minimal MRD in the patient is higher than 1 in 1000 cells.

25. The method of claim 1, wherein the patient has received allotransplantation.

26. The method of claim 1, wherein the patient is a pediatric or young adult patient.

27. The method of claim 1, wherein Compound A is administered in combination with one checkpoint inhibitor.

28. The method of claim 1, wherein the anti-PD-1 antibody is nivolumab, pembrolizumab, or pidilizumab.

29. The method of claim 28, wherein the anti-PD-1 antibody is nivolumab.

30. The method of claim 1, wherein the anti-PD-L1 antibody is MEDI4736 or MPDL3280A.

31. The method of claim 1, wherein Compound A is administered in combination with two checkpoint inhibitors independently selected from an anti-CTLA-4 antibody, an anti-PD-1 antibody, and an anti-PD-L1 antibody.

32. The method of claim 29, wherein Compound A is administered in combination with an anti-CTLA-4 antibody and an anti-PD-1 antibody.

33. The method of claim 29, wherein Compound A is administered in combination with an anti-CTLA-4 antibody and an anti-PD-L1 antibody.

34. The method of claim 31, wherein the anti-CTLA-4 antibody is tremelimumab or ipilimumab.

35. The method of claim 31, wherein the anti-PD-1 antibody is nivolumab, pembrolizumab, or pidilizumab.

36. The method of claim 31, wherein the anti-PD-L1 antibody is MEDI4736 or MPDL3280A.

37. The method of claim 1, wherein Compound A, or a pharmaceutically acceptable salt or solvate thereof, is orally administered.

38. The method of claim 1, wherein Compound A, or a pharmaceutically acceptable salt or solvate thereof, is administered at an amount of from about 1 mg to about 5 mg per day.

39. The method of claim 38, wherein Compound A, or a pharmaceutically acceptable salt or solvate thereof, is administered at an amount of about 1 mg per day.

40. The method of claim 38, wherein Compound A, or a pharmaceutically acceptable salt or solvate thereof, is administered at an amount of about 2 mg per day.

41. The method of claim 38, wherein Compound A, or a pharmaceutically acceptable salt or solvate thereof, is administered at an amount of about 3 mg per day.

42. The method of claim 38, wherein Compound A, or a pharmaceutically acceptable salt or solvate thereof, is administered at an amount of about 4 mg per day.

43. The method of claim 38, wherein Compound A, or a pharmaceutically acceptable salt or solvate thereof, is administered at an amount of about 5 mg per day.

44. The method of claim 1, wherein Compound A, or a pharmaceutically acceptable salt or solvate thereof, is administered once daily for 28 consecutive days in a 28 days cycle.

45. The method of claim 1, wherein Compound A, or a pharmaceutically acceptable salt or solvate thereof, is administered once daily for 5 consecutive days followed by 2 days of no administration in a 28 days cycle.

46. The method of claim 1, wherein Compound A, or a pharmaceutically acceptable salt or solvate thereof, is administered once daily for 21 consecutive days followed by 7 days of no administration in a 28 days cycle.

47. The method of claim 1, further comprising administering a therapeutically effective amount of a second agent, wherein the second agent is 1) an anti-CD38 antibody, 2) an anti-CD19 antibody, 3) an anti-CD33 antibody, 4) an anti-CD20 antibody, 5) a FLT-3 inhibitor, or 6) a hypomethylating agent, or a combination thereof.

48. The method of claim 47, wherein the second agent is an anti-CD38 antibody.

49. The method of claim 48, wherein the anti-CD38 antibody is isatuximab.

50. The method of claim 47, wherein the second agent is an anti-CD19 antibody.

51. The method of claim 50, wherein the anti-CD19 antibody is blinatumomab.

52. The method of claim 47, wherein the second agent is an anti-CD33 antibody.

53. The method of claim 52, wherein the anti-CD33 antibody is SGN-CD33A or AMG 330.

54. The method of claim 47, wherein the second agent is an anti-CD20 antibody.

55. The method of claim 54, wherein the anti-CD20 antibody is rituximab.

56. The method of claim 47, wherein the second agent is a FLT-3 inhibitor.

57. The method of claim 56, wherein the FLT-3 inhibitor is midostaurin, gilteritinib, or quizartinib.

58. The method of claim 47, wherein the second agent is a hypomethylating agent.

59. The method of claim 58, wherein the hypomethylating agent is SGI-110, azacytidine, or decitibine.

60. The method of claim 2, wherein the hematological cancer is transformed lymphoma, Richter's transformation, Waldenstrom macroglobulinemia (WM) or plasmacytoma.

61. The method of claim 2, wherein the hematological cancer is B-cell acute lymphoblastic leukemia.

62. The method of claim 2, wherein the hematological cancer is human lymphotropic virus-type 1 (HTLV-1) leukemia.

63. The method of claim 2, wherein the hematological cancer is chronic myelogenous leukemia.

64. The method of claim 2, wherein the hematological cancer is diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, mantle cell lymphoma (MCL), AIDS-related lymphoma, follicular lymphoma, small lymphocytic lymphoma, T-cell/histiocyte rich large B-cell lymphoma, primary mediastinal large B-cell lymphoma (PMBCL), splenic marginal zone lymphoma, primary CNS lymphoma (PCNSL), cutaneous T-cell lymphoma (CTCL), peripheral T-cell Lymphoma (PTCL), NK/T-cell lymphoma, cutaneous B-cell lymphoma (CBCL), nodal marginal zone lymphoma, or ALK-positive large B-cell lymphoma.

65. The method of claim 64, wherein the diffuse large B-cell lymphoma is ALK-positive large B-cell lymphoma.

66. A method of treating or managing amyloidosis comprising administering to a patient in need thereof a therapeutically effective amount of Compound A of following formula, or a pharmaceutically acceptable salt or solvate thereof:

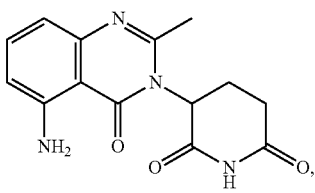 [SMILES: Cc1nc2cccc(N)c2c(=O)n1C1CCC(=O)NC1=O]

in combination with a therapeutically effective amount of one or more checkpoint inhibitor(s) selected from an anti-CTLA-4 antibody, an anti-PD-1 antibody and an anti-PD-L1 antibody.

67. A method of treating or managing scleroderma comprising administering to a patient in need thereof a therapeutically effective amount of Compound A of following formula, or a pharmaceutically acceptable salt or solvate thereof:

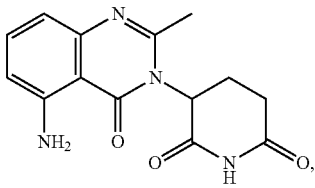 [SMILES: Cc1nc2cccc(N)c2c(=O)n1C1CCC(=O)NC1=O]

in combination with a therapeutically effective amount of one or more checkpoint inhibitor(s) selected from an anti-CTLA-4 antibody, an anti-PD-1 antibody and an anti-PD-L1 antibody.

68. A method of treating or managing myelodysplastic syndrome comprising administering to a patient in need thereof a therapeutically effective amount of Compound A of following formula, or a pharmaceutically acceptable salt or solvate thereof:

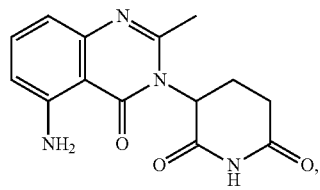 [SMILES: Cc1nc2cccc(N)c2c(=O)n1C1CCC(=O)NC1=O]

in combination with a therapeutically effective amount of one or more checkpoint inhibitor(s) selected from an anti-CTLA-4 antibody, an anti-PD-1 antibody and an anti-PD-L1 antibody.

69. A method of treating or managing mastocytosis comprising administering to a patient in need thereof a therapeutically effective amount of Compound A of following formula, or a pharmaceutically acceptable salt or solvate thereof:

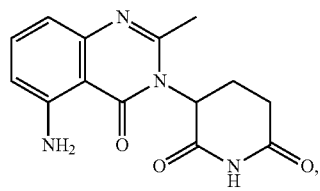 [SMILES: Cc1nc2cccc(N)c2c(=O)n1C1CCC(=O)NC1=O]

in combination with a therapeutically effective amount of one or more checkpoint inhibitor(s) selected from an anti-CTLA-4 antibody, an anti-PD-1 antibody and an anti-PD-L1 antibody.

* * * * *